US012066822B2

(12) United States Patent
Higashi

(10) Patent No.: US 12,066,822 B2
(45) Date of Patent: Aug. 20, 2024

(54) DEVICE FOR CONTROLLING GUIDANCE ROBOT, GUIDANCE SYSTEM IN WHICH SAME IS USED, AND METHOD FOR CONTROLLING GUIDANCE ROBOT

(71) Applicant: HONDA MOTOR CO., LTD., Tokyo (JP)

(72) Inventor: Haruomi Higashi, Saitama (JP)

(73) Assignee: HONDA MOTOR CO., LTD., Tokyo (JP)

( * ) Notice: Subject to any disclaimer, the term of this patent is extended or adjusted under 35 U.S.C. 154(b) by 277 days.

(21) Appl. No.: 17/415,174

(22) PCT Filed: Aug. 28, 2019

(86) PCT No.: PCT/JP2019/033721
§ 371 (c)(1),
(2) Date: Jun. 17, 2021

(87) PCT Pub. No.: WO2020/129311
PCT Pub. Date: Jun. 25, 2020

(65) Prior Publication Data
US 2022/0066438 A1  Mar. 3, 2022

(30) Foreign Application Priority Data

Dec. 19, 2018 (JP) ................................. 2018-237550

(51) Int. Cl.
| | |
|---|---|
| G05D 1/00 | (2006.01) |
| A61B 5/16 | (2006.01) |
| G05B 19/4155 | (2006.01) |
| G16H 40/67 | (2018.01) |
| A61B 5/00 | (2006.01) |
| A61B 5/01 | (2006.01) |
| A61B 5/11 | (2006.01) |

(52) U.S. Cl.
CPC ............ *G05D 1/0011* (2013.01); *A61B 5/165* (2013.01); *G05B 19/4155* (2013.01);
(Continued)

(58) Field of Classification Search
CPC .. G05D 1/0011; G05D 1/0212; G05D 1/0246; G05D 2201/0211; A61B 5/165;
(Continued)

(56) References Cited

U.S. PATENT DOCUMENTS

2010/0063627 A1* 3/2010 Kitahama ............ G05D 1/0246
                                                                  901/1
2018/0121936 A1* 5/2018 Madduri ............ G06Q 30/0201

FOREIGN PATENT DOCUMENTS

| JP | 2003-340764 | 12/2003 |
| JP | 2007-256228 | * 10/2007 |

(Continued)

OTHER PUBLICATIONS

Internation Search Report, Date of mailing: Nov. 19, 2019, 1 page.
(Continued)

*Primary Examiner* — Muhammad Shafi
(74) *Attorney, Agent, or Firm* — Rankin, Hill & Clark LLP

(57) ABSTRACT

A server (3) includes a route determination unit (3*f*1) that determines a route; a user dynamic data recognition unit (3*a*1) that recognizes, during guidance, user dynamic data; a guidance request estimation unit (3*c*) that estimates a guidance request of a user, based on the user dynamic data; a notification instruction unit (3*h*) that issues to a robot (2) an instruction for notification of inquiry information for inquiring about necessity of change of the route; and a reaction recognition unit (3*i*) that recognizes a reaction of the user to the notification. The route determination unit (3*f*1) determines a content of the change of the route, based on the guidance request, and determines whether the change of the route is performed, based on the reaction.

8 Claims, 20 Drawing Sheets

(52) U.S. Cl.
CPC ........... *G05D 1/0212* (2013.01); *G16H 40/67* (2018.01); *A61B 5/01* (2013.01); *A61B 5/11* (2013.01); *A61B 5/4266* (2013.01); *G05B 2219/50391* (2013.01)

(58) Field of Classification Search
CPC ........... A61B 5/01; A61B 5/11; A61B 5/4266; G05B 19/4155; G05B 2219/50391; G16H 40/67; G16H 20/30; G06Q 90/20; B25J 13/00; G01C 21/36; G08G 1/00; G08G 1/005
USPC ......................................................... 701/26
See application file for complete search history.

(56) References Cited

FOREIGN PATENT DOCUMENTS

| JP | 2007-260822 | | 10/2007 |
|---|---|---|---|
| JP | 2008-149399 A | * | 7/2008 |
| JP | 2008-149399 A | | 7/2008 |
| JP | 2008-307658 A | | 12/2008 |
| JP | 2010-271911 | | 12/2010 |
| JP | 2018-027613 | | 2/2018 |
| JP | 2018-081185 | | 5/2018 |
| WO | WO-2017-179285 | * | 10/2017 |
| WO | WO-2018/133073 | * | 7/2018 |

OTHER PUBLICATIONS

Japanese Office Action dated May 10, 2022, Application No. 2020-561150, 4 pages.

Japan Office Action dated Jan. 24, 2023, Japanese Application No. 2020-561150, English translation included, 6 pages.

Japanese Office Action dated Sep. 20, 2022 issued in Japanese application No. 2020-561150, which is the corresponding application of related U.S. Appl. No. 17/415,140; English machine translation included (6 pages).

* cited by examiner

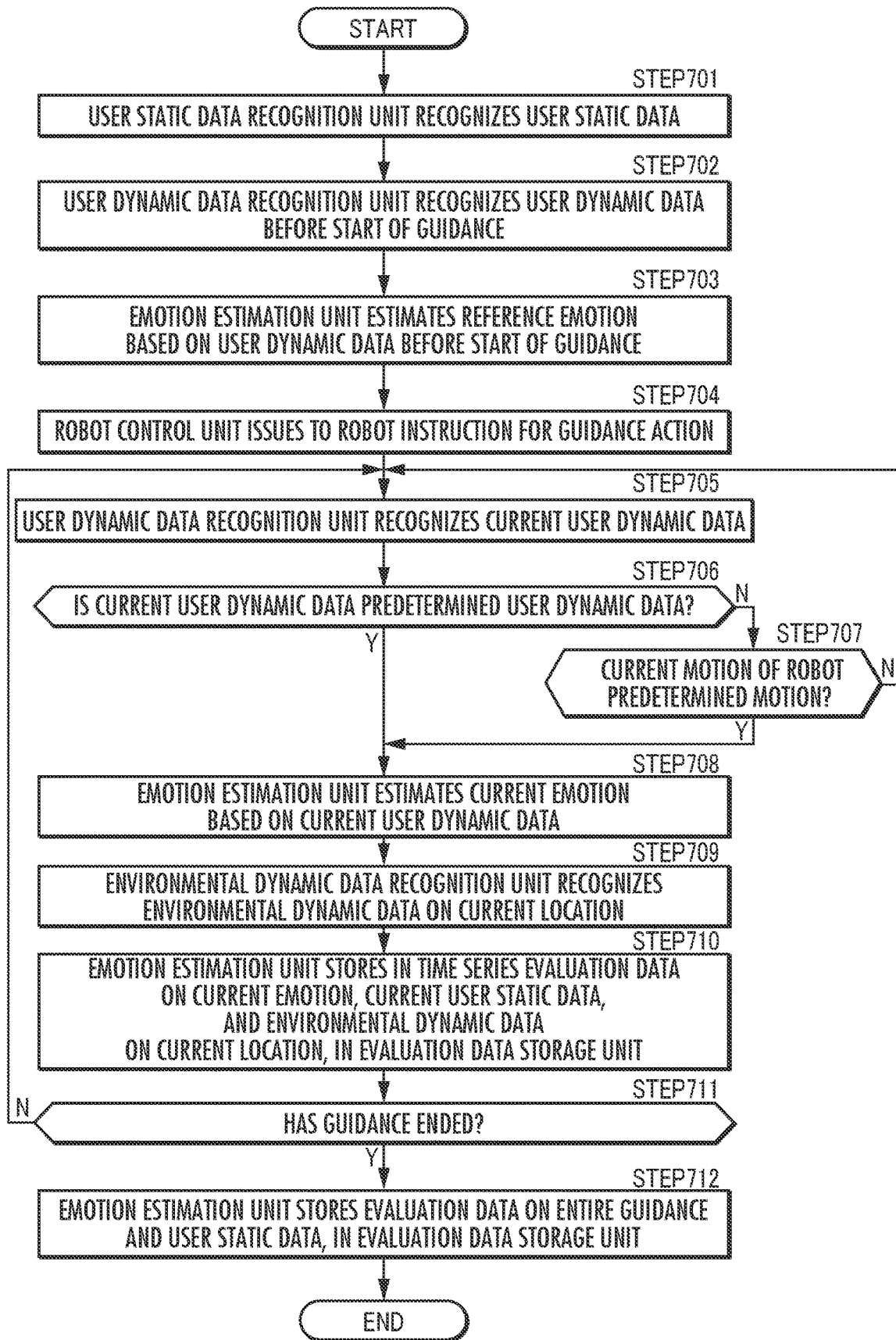

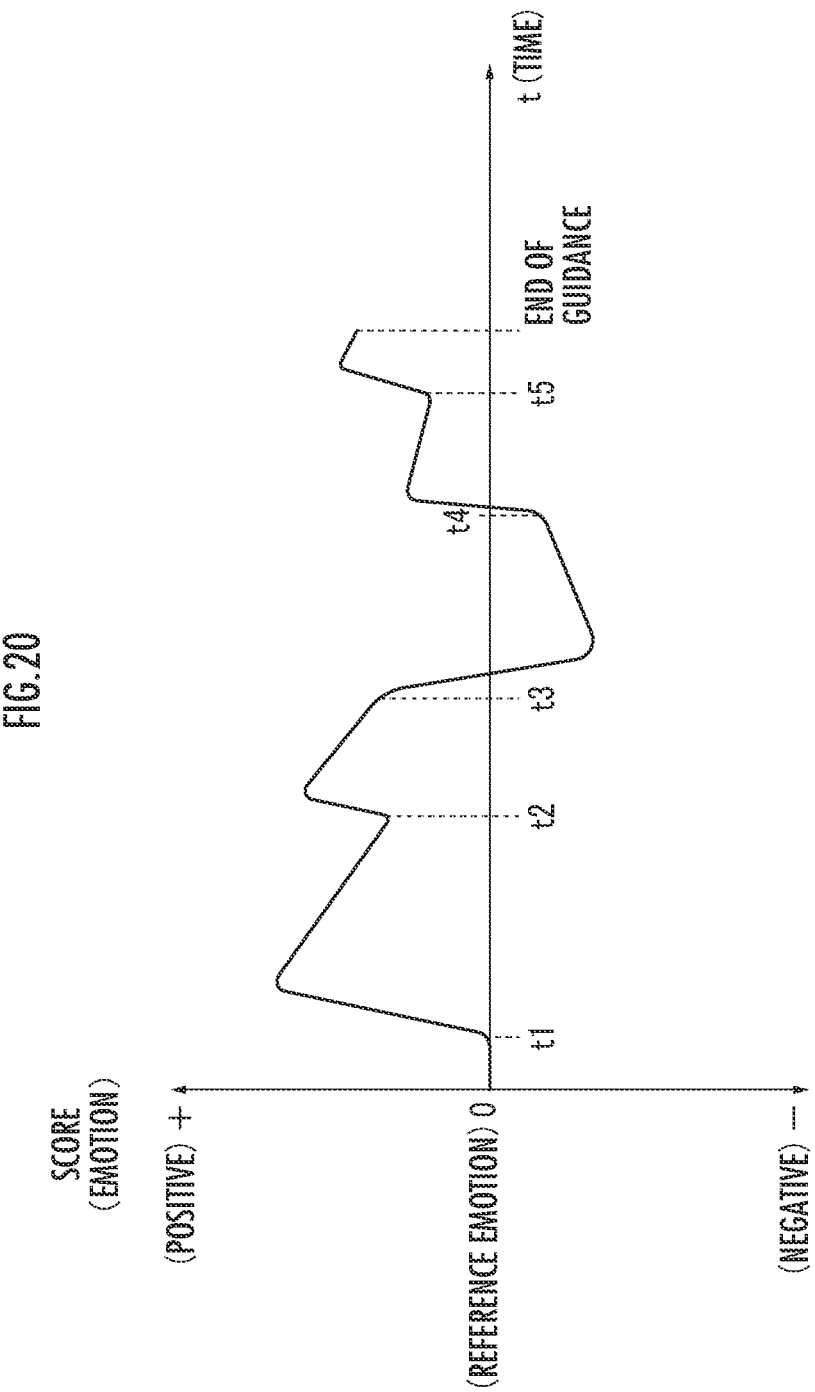

DEVICE FOR CONTROLLING GUIDANCE ROBOT, GUIDANCE SYSTEM IN WHICH SAME IS USED, AND METHOD FOR CONTROLLING GUIDANCE ROBOT

TECHNICAL FIELD

The present invention relates to a guide robot control device for controlling a robot that moves with a user and guides the user to a destination, a guidance system using the same, and a guide robot control method.

BACKGROUND ART

There has been conventionally proposed a guidance system that causes an autonomous mobile robot to move with a user to guide the user. A known guidance system of this type recognizes a walking speed and movement direction of the user by means of detection means such as a camera equipped in the robot and, based on the recognition result, controls the movement of the robot (see, for example, Patent Literature 1).

CITATION LIST

Patent Literature

Patent Literature 1: Japanese Patent Laid-Open No. 2003-340764

SUMMARY OF INVENTION

Technical Problem

The user in the case of being guided by the guidance system described in Patent Literature 1, moves with the recognition that the user is being guided by the robot, and accordingly the movement of the user corresponds to the movement of the robot.

However, some users, when moving in such a manner of being led by the robot, may feel that the user's action is restricted by the robot and may feel stressed.

The present invention has been made in view of the above, and an object of the present invention is to provide a guide robot control device capable of allowing a user to receive guidance with less stress, a guidance system using the same, and a guide robot control method.

Solution to Problem

A guide robot control device of the present invention is a guide robot control device for controlling a robot that
  moves with a user and guides the user to a destination,
  and the device comprises
a route determination unit that determines a route from a
  current location of the user to the destination,
a user dynamic data recognition unit that, during guidance, recognizes user dynamic data being information on the user that changes over time,
a guidance request estimation unit that estimates a guidance request of the user, based on the user dynamic data,
a notification instruction unit that issues to the robot an instruction for notification of inquiry information to the user for inquiring about necessity of change of the route, based on the determined route, and
a reaction recognition unit that recognizes a reaction of the user to the notification based on the instruction, and
the route determination unit determines a content of the change of the route, based on the estimated guidance request, and determines whether the change of the route is performed, based on the reaction.

Here. "user dynamic data" represents, of data on the user, data on things that change over time. Specifically, as described later, there may be mentioned a behavior of the user, biological information, and the like.

Furthermore, here. "guidance request" represents a users request with respect to the guidance. This guidance request includes not only a request clearly expressed by the user but also a request that the user potentially has.

In the guide robot control device of the present invention configured as described above, during the guidance (specifically, during the period from the start of the guidance to the end of the guidance), the route from the current location of the user to the destination is changed based on the estimated guidance request of the user. That is, the route for the guidance is determined based on not only a guidance request clearly expressed by the user but also a guidance request that the user potentially has.

As a result, the route becomes suitable for the guidance request of the user. For example, a facility that the user needs to use (for example, a break room, a toilet), and a position of a store where goods and services of interest to the user are provided are taken into consideration.

Furthermore, this guide robot control device inquires of the user about the necessity of the change of the route. This prevents the change of the route against the user's intention.

Thus, according to the guide robot control device of the present invention, the route for the guidance corresponds to the guidance request of the user, and the change of the route is performed while respecting the user's intention, so that the user can receive the guidance with less stress.

Furthermore, in the guide robot control device of the present invention, preferably,
  the route determination unit estimates a change in required time of the route before and after the change, and
  the notification instruction unit issues an instruction for notification of at least one of the change in the required time and arrival time to the destination in a case where the route is changed.

Thus, in the case of specifically notifying the user of the influence of the change of the route, the user can facilitate determination on the necessity of the change of the route. Consequently, the reaction of the user is made noticeable, so that the reaction of the user (that is, the user's intention on the necessity of the change of the route) can be recognized by the reaction recognition unit with high accuracy.

Accordingly, the user's intention on the necessity of the change of the route can be recognized with high accuracy, so that it becomes easier to determine whether the change of the route is performed in line with the user's intention. As a result, the user can receive the guidance with lesser stress.

Furthermore, in the guide robot control device of the present invention,
  the user dynamic data may be data including at least one of a behavior of the user and biological information of the user.

Furthermore, in the guide robot control device of the present invention, in the case where the user dynamic data includes at least one of the behavior of the user and the biological information of the user, the behavior of the user may include at least one of a movement speed of the user, a posture of the user, an expression of the user, an utterance of the user, and a motion of a predetermined portion of a body of the user.

Furthermore, in the guide robot control device of the present invention, in the case where the user dynamic data includes at least one of the behavior of the user and the biological information of the user, the biological information of the user may include at least one of a body temperature of the user, a sweating state of the user, and an emotion of the user estimated based on at least one of the body temperature of the user, the sweating state of the user, and the behavior of the user.

Furthermore, in the guide robot control device of the present invention, preferably, there is provided a priority storage unit that stores priority on facilities in a guidance area, and the route determination unit performs the change of the route, based on the estimated guidance request and the priority.

It may be difficult to determine only based on the request of the user which facility should be selected from a plurality of facilities with similar functions. On the other hand, among facilities in the guidance area with similar functions, there may be facilities that the user is desired to preferentially use and facilities that the user is desired not to use if possible.

For example, in the case of toilets at a place that is likely to be congested and a place that is less likely to be congested, from the standpoint of the management side of the guidance area, the preferential use of the place that is less likely to be congested is demanded.

Accordingly, as described above, in the case where priority of facilities is determined in advance and the priority is referred to when the route is changed, a demand from not only the user but also the facility side of the guidance area can be satisfied.

Furthermore, a guidance system of the present invention comprises a robot that moves with a user and guides the user to a destination, and the guide robot control device according to any of the above, and the guide robot control device has a robot control unit that moves the robot along the route.

Furthermore, a guide robot control method of the present invention is a guide robot control method for controlling a robot that moves with a user and guides the user to a destination, and the method comprises a step in which a route determination unit determines a route from a current location of the user to the destination, a step in which a user dynamic data recognition unit recognizes, during guidance, user dynamic data being information on the user that changes over time.

a step in which a guidance request estimation unit estimates a guidance request of the user, based on the user dynamic data.

a step in which a notification instruction unit issues to the robot an instruction for notification of inquiry information to the user for inquiring about necessity of change of the route, based on the determined route, a step in which a reaction recognition unit recognizes a reaction of the user to the notification based on the instruction, a step in which the route determination unit determines a content of the change of the route, based on the estimated guidance request, and a step in which the route determination unit determines whether the change of the route is performed, based on the reaction.

BRIEF DESCRIPTION OF DRAWINGS

FIG. 19 is a flowchart illustrating processing that the guidance system of FIG. 1 performs when estimating evaluation.

FIG. 20 is a graph illustrating an example of a change in emotion of the user, in which the horizontal axis indicates time and the vertical axis indicates a degree of whether the emotion is negative or positive.

DESCRIPTION OF EMBODIMENT

Hereinafter, a configuration of a guidance system S according to an embodiment will be described with reference to the drawings.

In the following description, a case will be described in which a guidance area which is an area where a user is guided by a robot is an airport, and in which a guide robot control device, guidance system using the same, and guide robot control method of the present invention are applied to a system for guiding the user in the airport.

However, the guide robot control device, guidance system using the same, and guide robot control method of the present invention may be applied to a system that is used in a guidance area other than an airport as long as the system is for performing guidance by using a robot that moves with a user and guides the user to a destination.

First, a schematic configuration of the guidance system S will be described with reference to FIGS. 1 to 6.

Figure 1:
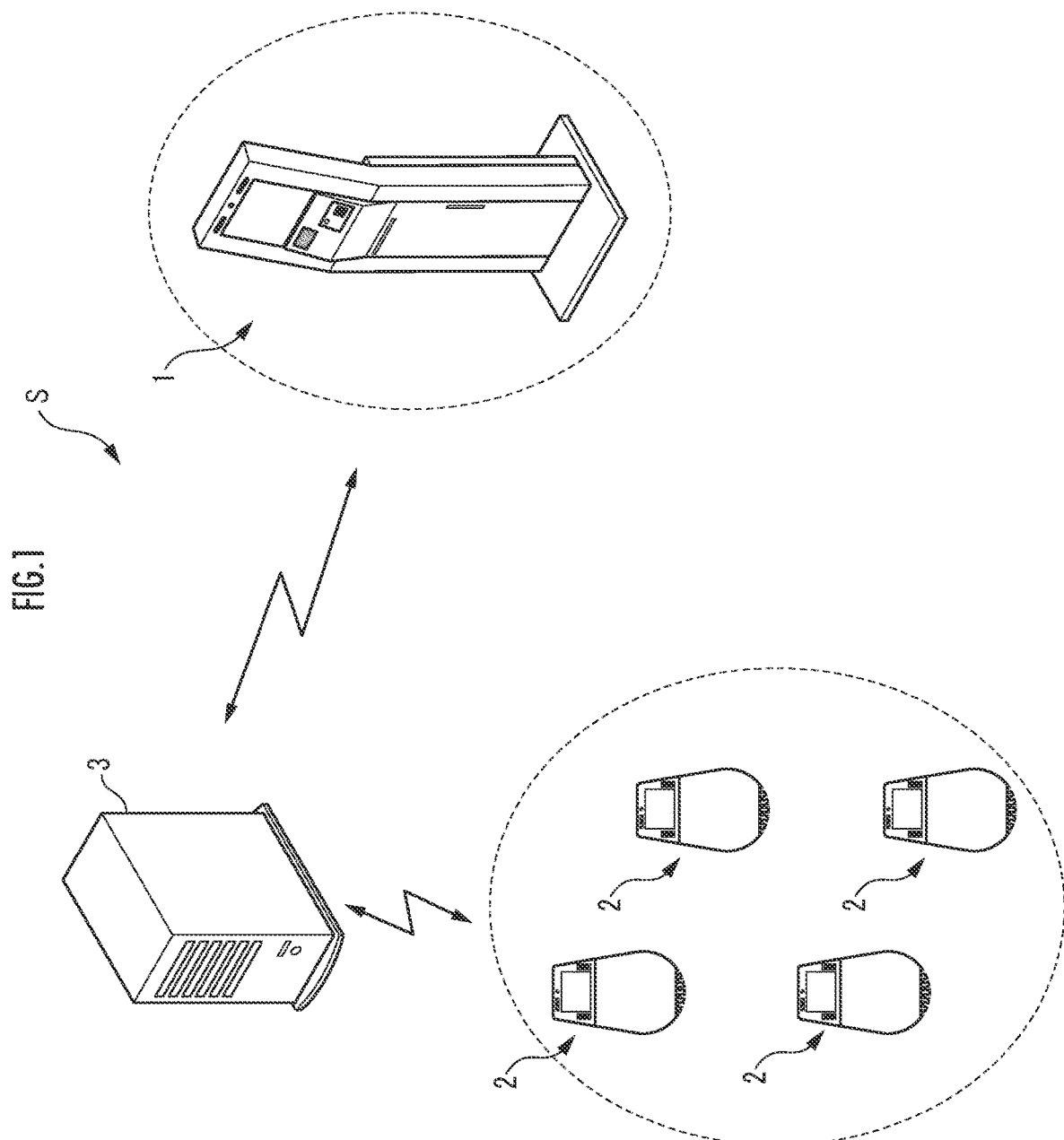
FIG. 1 is an explanatory view schematically illustrating a configuration of a guidance system according to an embodiment.

As illustrated in FIG. 1, the guidance system S comprises a reception terminal 1, a plurality of robots 2 that each moves with a user and guides the user to a destination, and a server 3 (guide robot control device) that receives information from the reception terminal 1 (see FIG. 7) installed in a plurality of locations in an airport serving as a guidance area, the robot 2, and a monitoring system 4 (not illustrated in FIG. 1, see FIG. 3) including a monitoring camera or the like installed in the guidance area, and that controls the robot 2 based on the information.

In the present embodiment, for facilitation of the understanding, the reception terminal 1 is installed in the airport serving as the guidance area, and the plurality of robots 2 is operated. However, the guidance system of the present invention is not limited to such a configuration. For example, a portable terminal of the user (for example, a smartphone, a tablet) may be used instead of the reception terminal 1 or may be used in combination therewith.

Furthermore, the number of the reception terminals and the number of the robots may be set as necessary according to properties of the guidance area (the size, the number of the users, and the like). For example, in the case of a facility having a smaller guidance area, one reception terminal and one robot may be provided, or only one robot may be installed and only a portable terminal of the user may be used instead of the reception terminal.

The reception terminal 1 is a terminal for accepting an application that the user desires the use in the guidance area.

Figure 2:
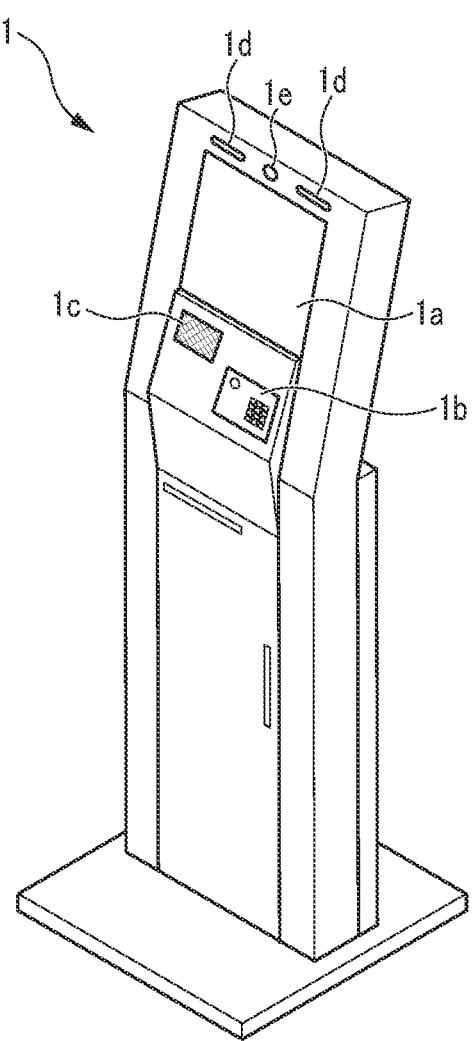
FIG. 2 is a side view illustrating an example of a reception terminal of the guidance system of FIG. 1.

As illustrated in FIG. 2, the reception terminal 1 comprises a first touch panel 1a, a keyboard 1b, a first microphone 1c, a first speaker 1d, and a first camera 1e. In the reception terminal 1, an input unit includes the first touch panel 1a, the keyboard 1b, and the first microphone 1c, and an output unit includes the first touch panel 1a and the first speaker 1d.

The user, via the input unit of the reception terminal 1, inputs a destination and a desired arrival time to the destination and answers a questionnaire displayed on the output unit of the reception terminal 1. As contents of the questionnaire, for example, there may be mentioned a name, age, gender, chronic disease, presence or absence of disability, pregnancy status, presence or absence of companion, a past use history, and a course of the user to arrive at the guidance area. During this input and answer, the user is photographed by the first camera 1e.

These pieces of information may be input via a terminal owned by the user (for example, a personal computer, a smartphone, a tablet), before arrival at the guidance area, during a flight reservation, or the like.

Furthermore, these pieces of information may be input at timings different for each information by using in combination the reception terminal 1 and the terminal owned by the user. Specifically, for example, a barcode indicating information such as a name of the user, a flight to be used, a boarding gate, and boarding time may be presented on a boarding pass for an aircraft, and the user may read the barcode by using a barcode reader provided in the reception terminal 1, a camera equipped in the terminal owned by the user, or the like to input the information.

Figure 3:
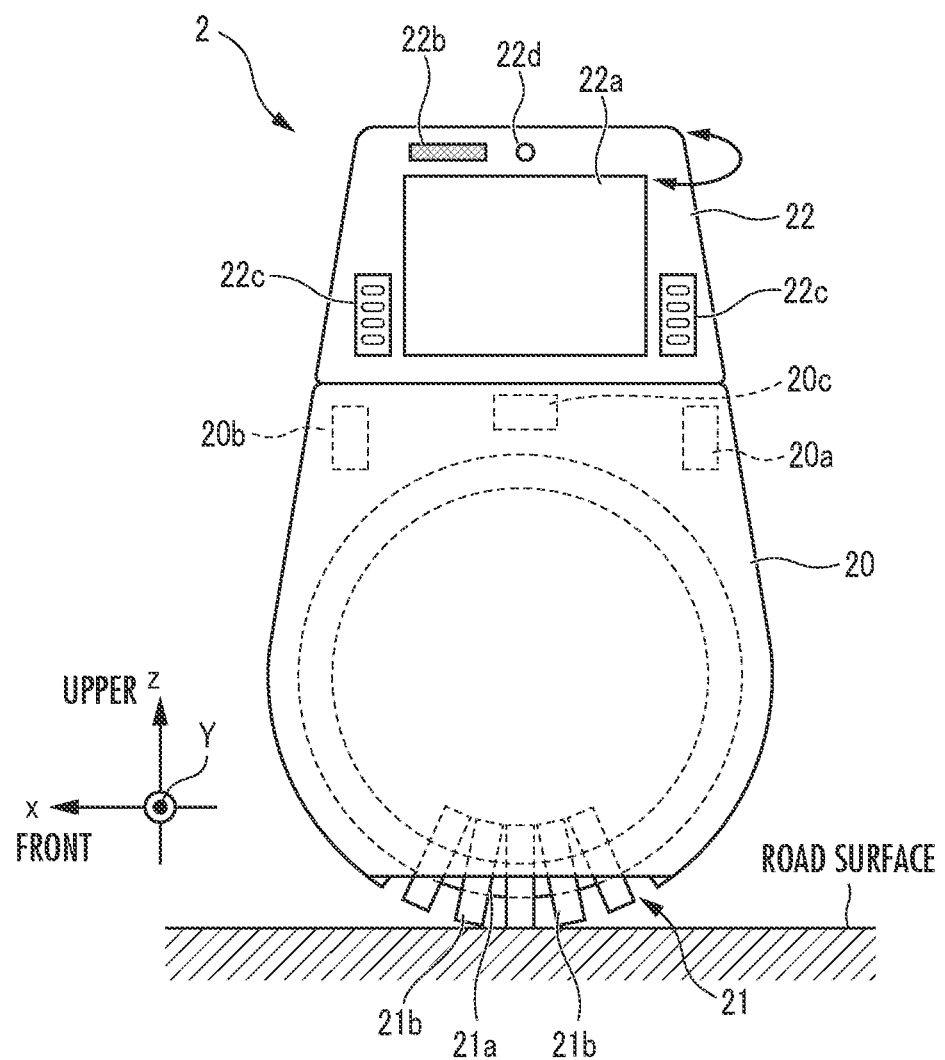
FIG. 3 is a side view illustrating an example of a robot of the guidance system of FIG. 1.

As illustrated in FIG. 3, the robot 2 is configured as a so-called inverted pendulum vehicle. The robot 2 comprises a lower base 20, a moving motion unit 21 provided in the lower base 20 and movable on a road surface, and an upper base 22 pivotable with respect to the lower base 20 around the yaw axis. The robot 2 is configured to be capable of moving on the road surface in all directions (any direction) by means of the moving motion unit 21.

The inside of the lower base 20 is equipped with a first actuator 20a that rotationally drives a core body 21a of the moving motion unit 21, which will be described later, a second actuator 20b that rotationally drives each of rollers 21b of the moving motion unit 21, which will be described later, and a third actuator 20c that pivots the upper base 22. Each of these actuators includes a known structure such as an electric motor or a hydraulic actuator.

Furthermore, the first actuator 20a, the second actuator 20b, and the third actuator 20c respectively apply a driving force to the core body 21a, each of the rollers 21b, and the upper base 22 via a power transmission mechanism, which is not illustrated. This power transmission mechanism includes a known structure.

The moving motion unit 21 has the core body 21a having an annular shape, and a plurality of the rollers 21b having an annular shape and inserted into the core body 21a from outside such that the plurality of rollers 21b is arranged at equal angular intervals in the circumferential direction of this core body 21a (axial center circumferential direction). In FIG. 3, only some of the rollers 21b are illustrated representatively.

Each of the rollers 21b is rotatable integrally with the core body 21a around an axial center of the core body 21a. Furthermore, each of the rollers 21b is rotatable around a central axis of a cross section of the core body 21a at the arrangement position of each of the rollers 21b (an axis in the tangential direction of a circumference centered on the axial center of the core body 21a).

The moving motion unit 21 configured as described above is movable on the road surface in all directions by one or both of rotational driving of the core body 21a around its axial center and rotational driving of each of the rollers 21b around its axial center, in the state where the rollers 21b at a lower part of the moving motion unit 21 are in contact with the road surface (a floor surface, a ground surface, or the like) in a movement environment of the robot 2.

The upper base 22 comprises a second touch panel 22a, a second microphone 22b, and a second speaker 22c. In the upper base 22, an input unit includes the second touch panel 22a and the second microphone 22b, and an output unit includes the second touch panel 22a and the second speaker 22c.

The upper base 22, via the output unit thereof, presents a change of a guidance content to the user. Furthermore, the user, via the input unit thereof, inputs an answer to the proposal and a request for the change of the guidance content.

Furthermore, the upper base 22 is provided with a second camera 22d. The user and environments around the user and the robot 2 are photographed by this second camera 22d.

Figure 4:
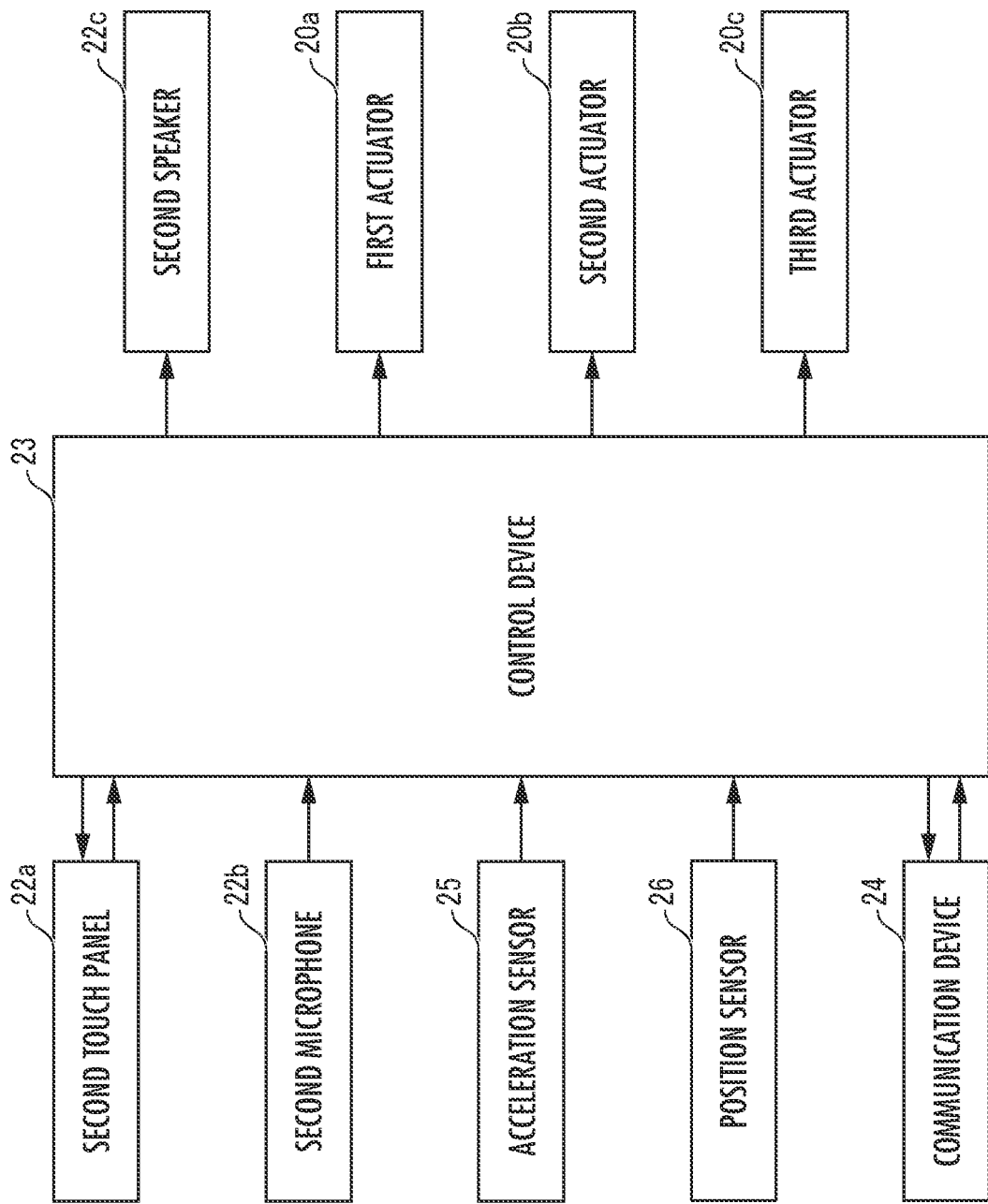
FIG. 4 is a block diagram illustrating a configuration according to motion control of the robot of FIG. 3.

Furthermore, although not illustrated in FIG. 3, as illustrated in FIG. 4, the robot 2 is equipped with various sensors for acquiring an instruction of the user, a motion state or external state (surrounding environment) of the robot 2, and the like, and is equipped with, as components for motion control of the robot 2, a control device 23 formed of an electronic circuit unit including a CPU, a RAM, a ROM, an interface circuit, and the like, and a communication device 24 for performing wireless communication between the server 3 and the control device 23.

The various sensors equipped in the robot 2 include the second touch panel 22a and the second microphone 22b that are for accepting an instruction of the user, and the second camera 22d as an external recognition sensor for recognizing objects (humans, moving objects, installed objects, and the like) present in the surrounding environment of the robot 2.

The external recognition sensor may be any sensor that can recognize the surrounding environment of the robot 2 during the guidance and at least one of a behavior of the user and biological information of the user. Accordingly, as the external recognition sensor, instead of the second camera 22d or in addition to the second camera 22d, for example, a distance measuring sensor such as a laser range finder, or a radar device may be used.

Furthermore, in the case where the robot 2 additionally comprises, independently of the second camera 22d, a sensor for controlling a behavior of the robot 2 (for example, a camera for photographing in the traveling direction), the sensor, instead of the second camera 22d or in addition to the second camera 22d, may be used as the external recognition sensor.

Here, specifically, "during guidance" represents a period from the start of the guidance to the end of the guidance. Furthermore. "before start of guidance" represents a stage before the guidance by the robot 2 is executed. For example, it also includes a period from when the user performs an input to the reception terminal 1 or when the user arrives at the guidance area, until before the user and the robot 2 meet.

The behavior of the user represents one including at least one of a movement speed of the user, a posture of the user, an expression of the user, an utterance of the user, and a motion of a predetermined portion of a body of the user. Furthermore, the biological information of the user represents one including at least one of a body temperature of the user, a sweating state of the user, and an emotion of the user estimated based on at least one of the body temperature of the user, the sweating state of the user, and the behavior of the user.

Furthermore, although not illustrated in FIG. 3, the various sensors also include an acceleration sensor 25 for detecting acceleration of the robot 2, a position sensor 26 for detecting a self-position of the robot 2 and a position of the user being guided by the robot 2, and the like.

Outputs (detection data) of the second touch panel 22a, the second microphone 22b, the acceleration sensor 25, the position sensor 26, and the like are input to the control device 23.

The control device 23 has, as functions to be implemented by installed hardware configurations or programs (software configurations), a function of performing motion control of the first actuator 20a, second actuator 20b, and third actuator 20c (consequently, movement control of the moving motion unit 21 and pivot control of the upper base 22), and a function of performing output control of the second touch panel 22a and second speaker 22c.

The communication device 24 transmits to the server 3 the outputs (detection data) of the various sensors and control contents of the control device 23. Furthermore, the communication device 24 receives an instruction of the server 3.

Figure 5:
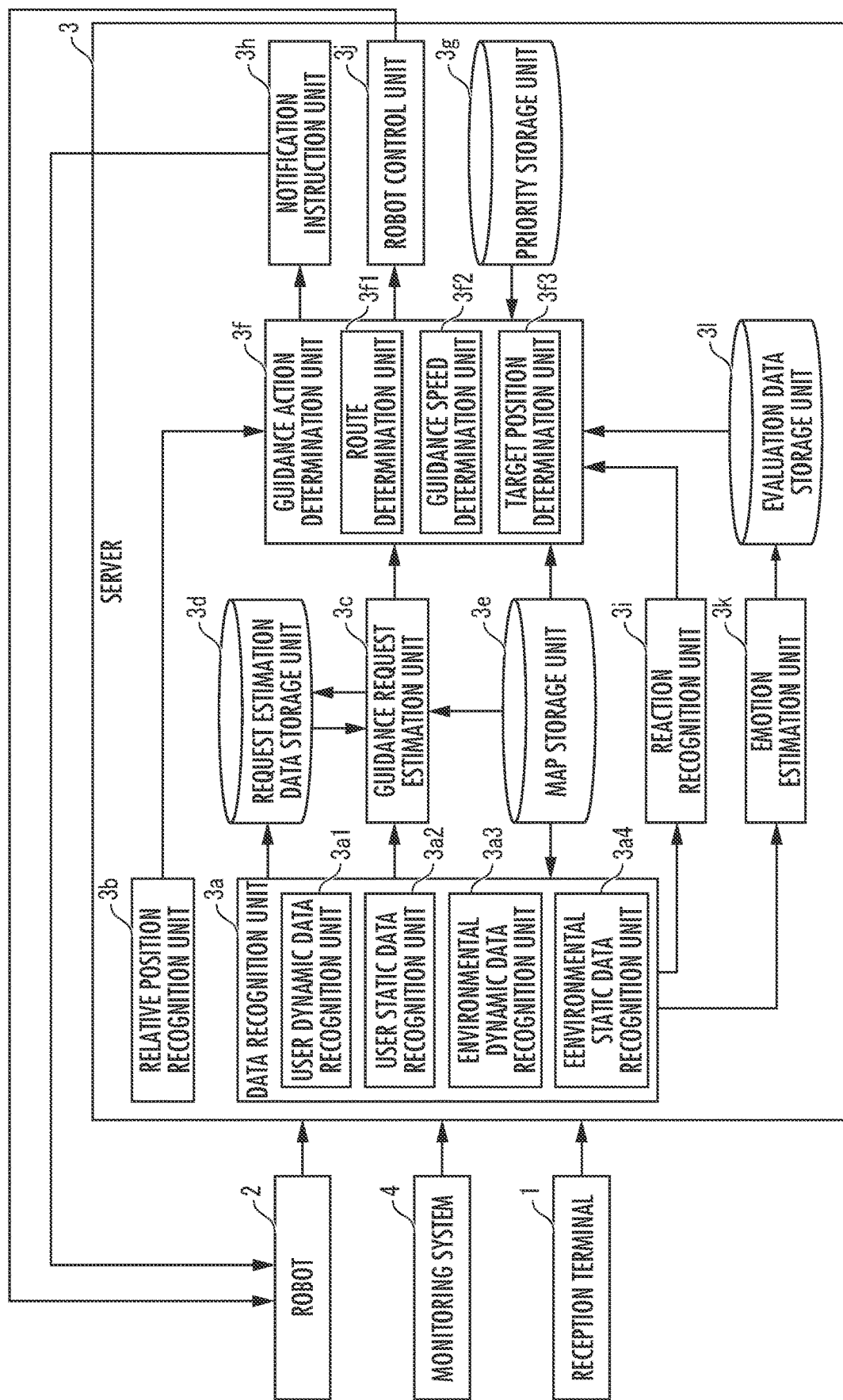
FIG. 5 is a block diagram illustrating a configuration of a guide robot control device of the guidance system of FIG. 1.

As illustrated in FIG. 5, the server 3 comprises, as functions to be implemented by installed hardware configurations or programs, a data recognition unit 3a, a relative position recognition unit 3b, a guidance request estimation unit 3c, a request estimation data storage unit 3d, a map storage unit 3e, a guidance action determination unit 3f, a priority storage unit 3g, a notification instruction unit 3h, a reaction recognition unit 3i, a robot control unit 3j, an emotion estimation unit 3k, and an evaluation data storage unit 3l.

The data recognition unit 3a recognizes data on the user and the guidance area before the start of the guidance and during the guidance, based on information collected via the reception terminal 1, the robot 2, and the monitoring system 4.

Specifically, the data recognition unit 3a, by means of a user dynamic data recognition unit 3a1, recognizes user dynamic data being information on the user that changes over time, based on an image captured by the reception terminal 1 or the robot 2 and a sound acquired by the reception terminal 1 or the robot 2.

Here, "user dynamic data" represents, of data on the user, data on things that change over time (for example, things that change during the guidance). Specifically, there may be mentioned a behavior of the user, biological information, and the like.

The user dynamic data recognition unit 3a1 also determines whether the recognized user dynamic data is predetermined user dynamic data serving as a trigger of change of the guidance content or emotion estimation.

Furthermore, the data recognition unit 3a, by means of a user static data recognition unit 3a2, recognizes user static data being information on the user that does not change over time, based on a content input by the user to the reception terminal 1 and an answer to the questionnaire presented via the reception terminal 1.

Here, "user static data" represents, of data on the user, data on things that do not change over time (for example, things that do not change during the guidance). For example, there may be mentioned information on attributes of the user such as a name, age, gender, chronic disease, presence or absence of disability, pregnancy status, and presence or absence of companion, and, of data on actions of the user such as arrival time to a destination to which the user requests to be guided, a past guidance history of the user, and a course of the user to arrive at the guidance area, things that do not change depending on the future actions of the user.

Furthermore, the data recognition unit 3a, by means of an environmental dynamic data recognition unit 3a3, recognizes environmental dynamic data being information on the guidance area that changes over time, based on an image captured by the robot 2 and a sound acquired by the robot 2.

Here, "environmental dynamic data" represents, of data on the environment of the guidance area, data on things that change over time (for example, things that change during the guidance). For example, there may be mentioned an event such as a degree of congestion in the guidance area.

The environmental dynamic data recognition unit 3a3 also determines whether the recognized environmental dynamic data is predetermined environmental dynamic data serving as a trigger of change of the guidance content or emotion estimation.

Furthermore, the data recognition unit 3a, by means of an environmental static data recognition unit 3a4, recognizes environmental static data being information on the guidance area that does not change over time, based on information from the map storage unit 3e, which will be described later.

Here, "environmental static data" represents, of data on the environment of the guidance area, data on things that do not change over time (for example, things that do not change during the guidance). For example, there may be mentioned positions of a store and a facility in the guidance area and an event being held.

The relative position recognition unit 3b recognizes a relative position of the robot 2 with respect to the user, based on information collected via the robot 2 and the monitoring system 4.

Here. "relative position" may represent only a distance from the user to the robot or only a direction in which the robot is located with respect to the user and also may represent a degree of a change in the relative position during turning or the like.

Furthermore, here. "direction" represents a direction of the robot with respect to the user in a plane parallel to movement surfaces of the user and the robot. For example, it represents, in the case where the user and the robot move on level ground, in a plan view, a slope (angle) of a line passing through the center of the body of the user and the center of the robot 2 with respect to a line passing through the center of the body of the user and extending in the front-rear direction (a line included in a sagittal plane) (see FIG. 14).

The relative position recognition unit 3b of the present embodiment recognizes, as the relative position, a distance from the user to the robot 2 and a direction in which the robot 2 is located with respect to the user, based on information collected by at least one of the robot 2 and the monitoring system 4.

The guidance request estimation unit 3c estimates a guidance request of the user before the start of the guidance and during the guidance, based on the user dynamic data, the user static data, the environmental dynamic data, and the environmental static data that are recognized by the data recognition unit 3a, request estimation data stored in the request estimation data storage unit 3d, which will be described later, and map information being information on the guidance area stored in the map storage unit 3e, which will be described later (specifically, of the map information, information on the vicinity of a current location of the user).

Here, "guidance request" represents a users request with respect to the guidance. This guidance request includes not only a request clearly expressed by the user but also a request that the user potentially has.

Thus, the guidance request estimation unit 3c estimates the guidance request of the user, based on the user dynamic data, the user static data, the environmental dynamic data, the environmental static data, the request estimation data, and the map information.

This is because in the case where, in addition to the user dynamic data, at least one of the user static data, the environmental dynamic data, and the environmental static data is referred to at the time of estimation of the guidance request of the user, the guidance action can be made more suitable for the user.

However, the guidance request estimation unit of the present invention may be any unit that estimates the guidance request of the user based on the user dynamic data. Accordingly, functions that the guide robot control device comprises may be changed as necessary according to the type of information that the guidance request estimation unit uses.

Specifically, for example, in the present embodiment, any of the user static data recognition unit 3a2, environmental dynamic data recognition unit 3a3, and environmental static data recognition unit 3a4 of the data recognition unit 3a, the request estimation data storage unit 3d, and the map storage unit 3e may be omitted.

Thus, the guidance request estimation unit 3c, before the start of the guidance and during the guidance, estimates the guidance request of the user. This is to ensure that the guidance action corresponds to the guidance request of the user from the start of the guidance.

However, the guidance request estimation unit of the present invention may be any unit that estimates the guidance request of the user during the guidance. Accordingly, estimation of the guidance request of the user before the start of the guidance may be omitted.

The request estimation data storage unit 3d stores the request estimation data indicating a relationship between the user dynamic data in the previous or earlier guidance and the guidance request estimated based on the user dynamic data. As described above, the guidance request estimation unit 3c refers to the request estimation data stored in the request estimation data storage unit 3d and estimates the guidance request of the user.

This is because some of the actions of the user with respect to the guidance request (that is, the user dynamic data) can be generalized, and thus by referring to such request estimation data, the guidance request of the user is estimated with high accuracy.

However, the guide robot control device of the present invention is not limited to such a configuration. For example, the request estimation data may not be referred to at the time of estimation of the guidance request of the user. In such a case, the request estimation data storage unit may be omitted.

Furthermore, the request estimation data storage unit 3d, upon the guidance request estimation unit 3c estimating the guidance request of the user, stores the request estimation data on the estimation.

This is because the request estimation data that can be referred to is accumulated to increase data that can be referred to at the time of the next or later estimation of the guidance request, so that the next or later estimation of the guidance request of the user is performed with even higher accuracy.

However, the guide robot control device of the present invention is not limited to such a configuration. For example, in the case where the request estimation data is separately prepared in advance, the request estimation data may not be stored upon the estimation.

The request estimation data is associated with the user static data on the user relating to the estimation. This is because at the time of the next or later reference to the request estimation data, the request estimation data associated with the user static data (attribute) similar to that of the user to be guided can be referred to, so that the guidance request is estimated more precisely.

The request estimation data may not be necessarily stored in association with the user static data. The reason is because, for example, in the case of a facility where the users' attributes are constant to some extent (for example, an event venue targeting a predetermined age group), even if the request estimation data that is referred to in such a manner is not limited, the guidance request of the user can be estimated with sufficient accuracy.

The map storage unit 3e stores the map information being information on the guidance area. As the map information, in addition to the map information on the guidance area, there may be mentioned information on facilities such as a toilet and a store that are installed in the guidance area, information on an event being held in the guidance area and construction taking place continuously, and the like. Furthermore, the information on the facility provided in the guidance area also includes average time of use of the facility.

The map information stored in the map storage unit 3e (specifically, of the map information, information on the vicinity of a current location of the user) is, as described above, referred to when the guidance request estimation unit 3c estimates the guidance request of the user.

This is to estimate the guidance request of the user with high accuracy by referring to the map information, because even in the case where the user's action (that is, the user dynamic data) is the same, the guidance request arising from the action may be different depending on the position in the guidance area.

However, the guide robot control device of the present invention is not limited to such a configuration. For example, the map information may not be referred to at the time of estimation of the guidance request of the user. In such a case, the map storage unit may be omitted.

The guidance action determination unit 3f determines the guidance action that the robot 2 performs at the start of the guidance and during the guidance, based on the environmental dynamic data recognized by the data recognition unit 3a, the relative position recognized by the relative position recognition unit 3b, and the guidance request estimated by the guidance request estimation unit 3c.

Here, "guidance action" represents, during the guidance, a content of a service to be provided from the robot 2 to the user and a condition for determining a motion of the robot 2. For example, in addition to a route at the time of the guidance, which will be described later in the present embodiment, a guidance speed being a movement speed of the robot 2 at the time of the guidance, a relative position of the robot 2 with respect to the user, and a content of information to be notified to the user, there may be mentioned a content such as a type of the robot that performs the guidance (for example, whether it is a robot that leads the user, whether it is a robot in which the user can ride).

Specifically, the guidance action determination unit 3f, based on the guidance request estimated by the guidance request estimation unit 3c, determines, at the start of the guidance, a route from the guidance start point to the destination, and changes, during the guidance, a route from the current location to the destination, by means of a route determination unit 3f1.

Furthermore, the route determination unit 3f1 also estimates a change in the required time before and after the change and arrival time to the destination. Then, the change in the required time and the arrival time are presented to the user via the output unit of the robot 2.

This is to enable the user to facilitate determination on necessity of the change of the route. Consequently, this is to make a reaction of the user noticeable, so that the reaction of the user (that is, the user's intention on the necessity of the change of the route) can be recognized by the reaction recognition unit 3i, which will be described later, with high accuracy.

The route determination unit of the present invention is not limited to such a configuration and may be any unit that can change the route based on the estimated guidance request. For example, one or both of the change in the required time before and after the change and the arrival time to the destination may not be estimated.

Furthermore, the guidance action determination unit 3f, by means of a guidance speed determination unit 3f2, determines a guidance speed at the start of the guidance and during the guidance, based on the guidance request estimated by the guidance request estimation unit 3c.

Furthermore, the guidance action determination unit 3f, by means of a target position determination unit 3f3, determines and changes, at the start of the guidance and during the guidance, a target position based on a relative position when the user starts to move after the robot 2 starts the guidance and the environmental dynamic data at the current location of the user.

The reason why not only a relative position set in advance at the start of the guidance but also the environmental dynamic data is thus referred to is because depending on the environmental dynamic data (that is, a dynamic environment of the guidance area such as a degree of congestion), a position different from a position that the user originally considers to be preferable may be used as a position at which the user is less likely to feel stress.

However, the target position determination unit of the present invention is not limited to such a configuration. For example, the target position may be determined or changed without reference to the environmental dynamic data.

Furthermore, the guidance action determination unit 3f, when determining or changing the guidance action that the robot 2 performs during the guidance, also refers to priority stored in the priority storage unit 3g, which will be described later.

This is because, for example, it may be difficult to determine only based on the request of the user which facility should be selected from a plurality of facilities with similar functions, while among facilities in the guidance area with similar functions, there may be facilities that the user is desired to preferentially use and facilities that the user is desired not to use if possible.

For example, in the case of toilets at a place that is likely to be congested and a place that is less likely to be congested, from the standpoint of the management side of the guidance area, the preferential use of the place that is less likely to be congested is demanded.

Accordingly, as described above, in the case where priority of facilities is determined in advance and the priority is referred to when the guidance action is determined or changed, a demand from not only the user but also the facility side of the guidance area can be satisfied.

As specific processing in the case where the priority is referred to, for example, there may be mentioned processing in which a route to be guided is set to a route through a facility with high priority, in which the guidance speed of the robot 2 is made slower in front of a facility with high priority, and in which the target position is set to a position that is less likely to prevent the user from recognizing a facility with high priority.

However, the guidance action determination unit of the present invention is not limited to such a configuration. For example, the priority may not be referred to in determination and change of every guidance action. In such a case, the priority storage unit may be omitted. Furthermore, the priority may be referred to only in determination and change of some of the guidance actions.

Furthermore, the guidance action determination unit 3*f*, when determining or changing the guidance action that the robot 2 performs during the guidance, also refers to, of evaluation data stored in the evaluation data storage unit 3*l*, which will be described later, evaluation data in the previous or earlier guidance.

This is because the guidance action is determined by referring to the evaluation data (for example, a guidance action that has caused a negative emotion in the evaluation data is not performed), so that the guidance action to be actually performed is made more suitable.

However, the guidance action determination unit of the present invention is not limited to such a configuration. For example, the evaluation data may not be referred to in determination and change of every guidance action. Furthermore, the evaluation data may be referred to only in determination and change of some of the guidance actions.

Furthermore, the guidance action determination unit 3*f*, when changing the guidance action that the robot 2 performs during the guidance, performs final determination on whether the guidance action is to be changed, based on a reaction of the user recognized by the reaction recognition unit 3*i*, which will be described later. As a result, the guidance action can be prevented from being suddenly changed.

However, the guidance action determination unit of the present invention is not limited to such a configuration. For example, the reaction of the user may not be referred to in determination and change of every guidance action. Furthermore, the reaction of the user may be referred to only in determination and change of some of the guidance actions.

The priority storage unit 3*g* stores the priority on facilities in the guidance area. This priority may be optionally set by a system designer of the guidance system S or the like.

For example, in the case of toilets at a place that is likely to be congested and a place that is less likely to be congested, from the standpoint of the management side of the guidance area, the preferential use of the place that is less likely to be congested is demanded. In the case where such a demand is grasped, the priority of the toilet that is less likely to be congested may be set to be higher than the priority of the toilet that is likely to be congested.

Furthermore, for example, since the guidance system S of the present embodiment is introduced to the airport, the priority of a facility important to the operation side of the airport (for example, a facility with high rent) may be made higher.

The notification instruction unit 3*h* issues to the robot 2 an instruction for notification of inquiry information to the user for inquiring about necessity of change of the guidance action, based on the determined guidance action (for example, the guidance route, the guidance speed, and the target position).

Specifically, the notification instruction unit 3*h* notifies of the content of the change of the guidance action, the change in the required time before and after the change, and the arrival time to the destination that are determined by the guidance action determination unit 3*f*, and instructs the robot 2 to perform the notification for inquiring about the necessity of the change. The robot 2 that has received this instruction performs the notification to the user via the output unit of the robot 2.

The reaction recognition unit 3*i* recognizes how the user has reacted to the notification based on the instruction issued by the notification instruction unit 3*h* to the robot 2.

Specifically, the reaction recognition unit 3*i* recognizes the reaction of the user, based on the user dynamic data recognized by the data recognition unit 3*a*.

The robot control unit 3*j* controls the motion of the robot 2, based on the guidance action determined by the guidance action determination unit 3*f*.

The emotion estimation unit 3*k*, based on the user dynamic data recognized by the data recognition unit 3*a*, estimates a current emotion being a current emotion of the user, at a plurality of time points during the guidance. Furthermore, based on the user dynamic data recognized by the data recognition unit 3*a*, a reference emotion of the user serving as a reference for grasping a change in the emotion is estimated at the start of the guidance. Then, the emotion estimation unit 3*k* generates evaluation data being data in which a motion of the robot 2 and the current emotion of the user at the time of the motion are associated with each other, based on the current emotion and the reference emotion.

Figure 6:
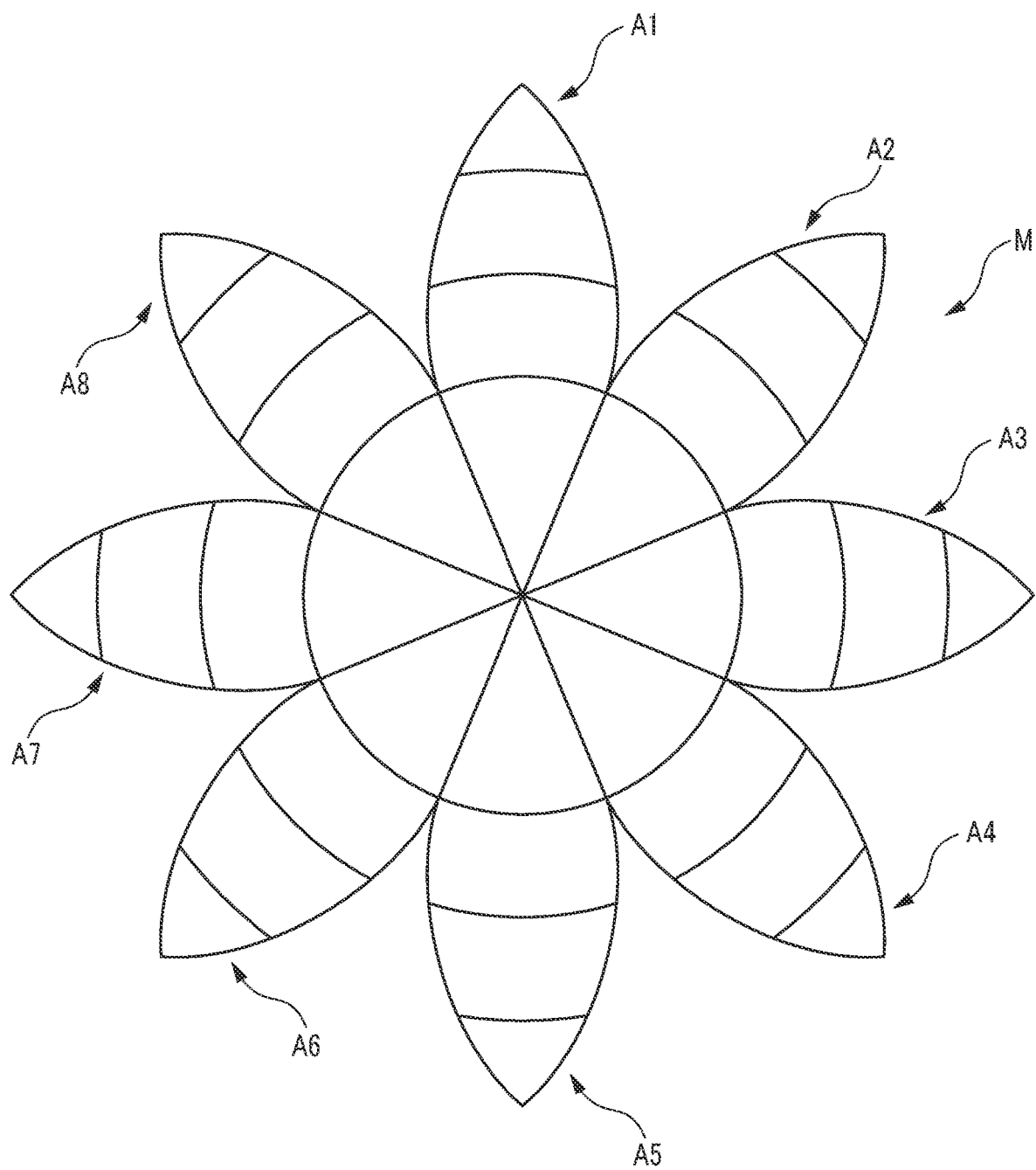
FIG. 6 is an explanatory view of an emotion model that is used in emotion estimation.

The emotion estimation of the emotion estimation unit 3*k* is performed based on, for example, a known or new emotion model. In the present embodiment, the emotion estimation is performed based on a known Plutchik emotion model M as illustrated in FIG. 6.

In this emotion model M, emotions are classified into four sets and eight types, and each of eight areas extending radially from the center corresponds to one of the emotions.

Specifically, a first area A1 corresponds to "joy"; a second area A2, "trust"; a third area A3. "fear"; a fourth area A4. "surprise"; a fifth area A5, "sadness"; a sixth area A6, "disgust"; a seventh area A7, "anger"; an eighth area A8. "anticipation." and the degree of the emotion is expressed to be stronger as it becomes closer to the center (to the inner area relative to the outer area).

As described above, this emotion estimation method is an example, and another method may be used. Specifically, an emotion model other than the Plutchik emotion model may be referred to. Furthermore, a data table may be used in which a motion and emotion of the user are associated with each other, or algorithm may be used in which a motion of the user is used as an input item and an emotion of the user is used as an output item.

The current emotion estimation of the emotion estimation unit 3*k* is performed at a plurality of time points during the guidance. Specifically, when it is determined based on the user dynamic data that a predetermined behavior is performed by the user, or when a predetermined motion is performed by the robot 2, the current emotion is estimated. This is because in the case where an emotion of the user is constantly estimated, it may be difficult to grasp which motion of the robot the emotion corresponds to.

The evaluation data storage unit 3*l* stores in time series the evaluation data generated by the emotion estimation unit 3*k*. As a result, regarding the emotional changes, data as in a graph illustrated in FIG. 20, which will be described later, is obtained.

The current emotion included in the evaluation data is associated with not only the current emotion itself but also whether the estimated emotion is a positive emotion or a negative emotion and the change in the emotion (as a result of the motion, whether it becomes favorable or worse, or the like).

In the present embodiment, the emotion estimation is performed based on the Plutchik emotion model M illustrated in FIG. 6, the eight areas of the emotion model M are classified as either positive or negative, and a score is set according to the area and the degree. Thus, the evaluation data storage unit 3*l* stores, in addition to the estimated emotion itself, the classification (that is, whether it is a positive emotion or a negative emotion) and a variation in the score (that is, the change in the emotion).

Furthermore, the evaluation data is also associated with the environmental dynamic data on the current location of the user at the time of the motion of the robot 2. This is because the environmental dynamic data also greatly affects the emotion of the user.

Furthermore, the evaluation data is also associated with the user static data on the user having been guided. This is because at the time of the next or later reference to the evaluation data, the evaluation data associated with the user static data (attribute) similar to that of the user to be guided can be referred to.

The evaluation data may not be necessarily associated with the environmental dynamic data and the user static data. Specifically, at least one of the environmental dynamic data and the user static data may not be associated with the evaluation data.

The configuration described with reference to FIG. 5 is an example of the guidance system of the present invention. That is, the functions to be implemented by the hardware configurations or programs installed in the server 3 in the present embodiment are not necessarily implemented by a single server.

For example, they may be implemented by using hardware configurations or programs installed in a plurality of servers or may be implemented by the hardware configurations or programs installed in the server in cooperation with hardware configurations or programs installed in at least one of the reception terminal, the robot, and the monitoring system. Furthermore, for example, without using the server, they may be implemented in cooperation with hardware configurations or programs installed in the plurality of robots or the monitoring system.

Next, processing that the server 3 of the guidance system S performs will be described with reference to FIGS. 5 and 7 to 20.

First, processing that the server 3 of the guidance system S performs when determining the guidance route at the start of the guidance and when changing the guidance mute during the guidance will be described with reference to FIGS. 5 and 7 to 10.

Figure 7:
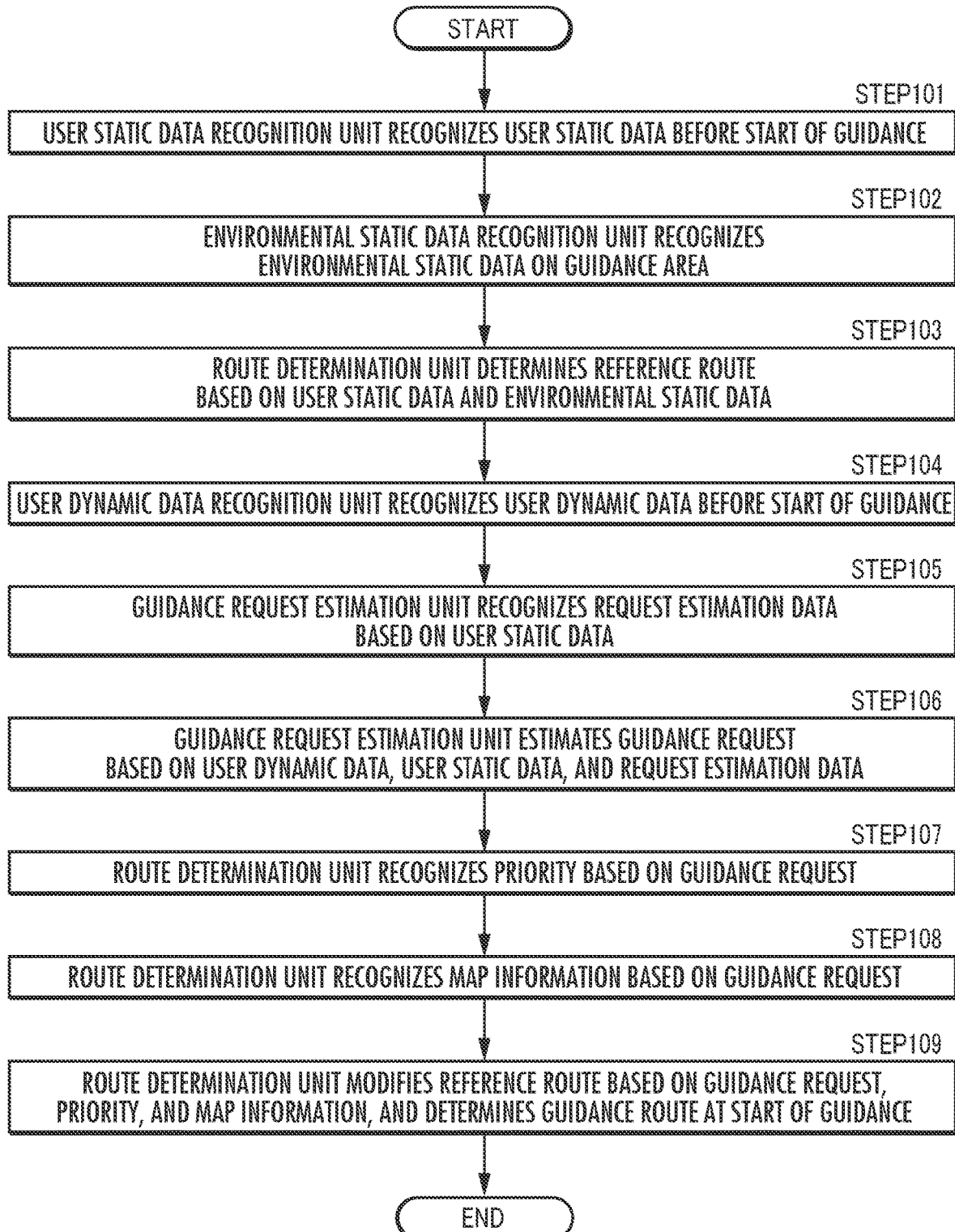
FIG. 7 is a flowchart illustrating processing that the guidance system of FIG. 1 performs when determining a guidance route at start of guidance.
Figure 9:
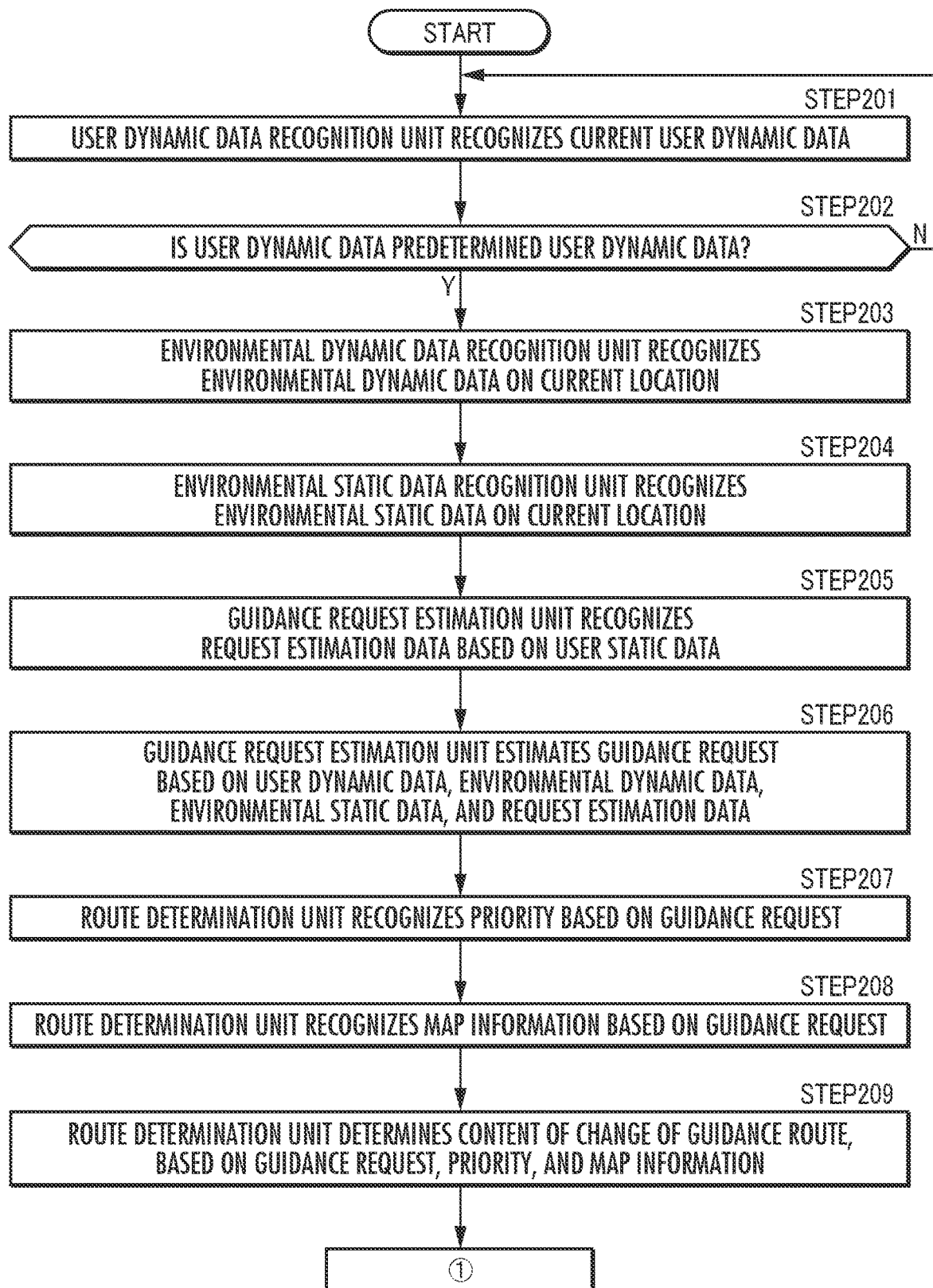
FIG. 9 is a flowchart illustrating, of processing that the guidance system of FIG. 1 performs when changing a guidance route during guidance, processing until a content of the change of the guidance route is determined.
Figure 10:
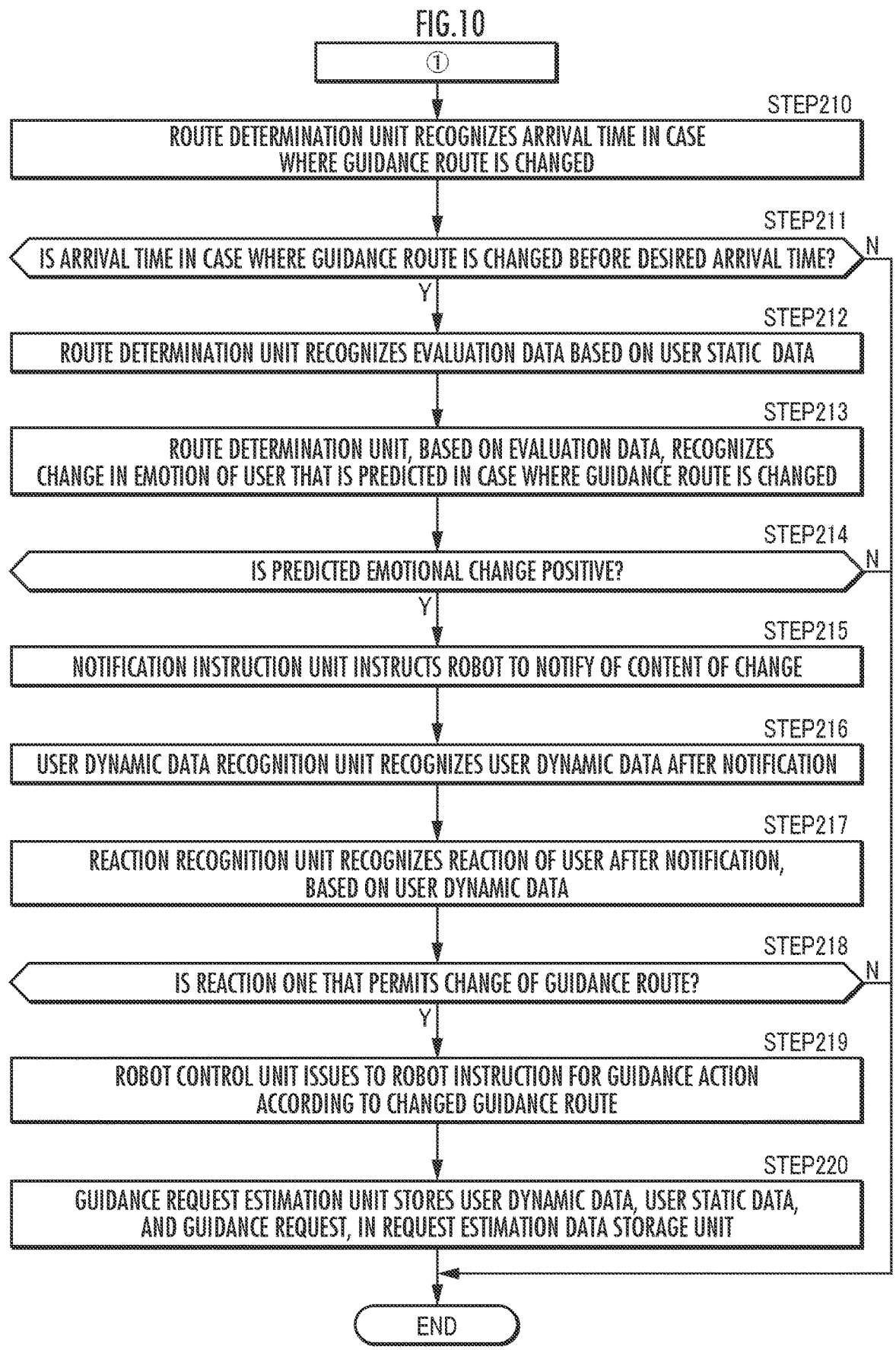
FIG. 10 is a flowchart illustrating, of the processing that the guidance system of FIG. 1 performs when changing a guidance route during guidance, processing until the change of the guidance route is executed.

FIG. 7 is a flowchart illustrating the processing that the server 3 of the guidance system S performs when determining the guidance route at the start of the guidance. Furthermore, FIG. 9 is a flowchart illustrating, of the processing that the server 3 of the guidance system S performs when changing the guidance route during the guidance, processing until a content of the change of the guidance route is determined. Furthermore, FIG. 10 is a flowchart illustrating, of the processing that the server 3 of the guidance system S performs when changing the guidance route during the guidance, processing until the change of the guidance route is executed.

First, the processing that the guidance system S performs when determining a guidance route at the start of the guidance will be described.

In this processing, the user static data recognition unit 3*a*2 of the data recognition unit 3*a* of the server 3 first recognizes the user static data before the start of the guidance (STEP 101 in FIG. 7).

Specifically, the reception terminal 1 installed at a guidance start location P0 first recognizes information input by the user at the time of reception, information on the reception terminal 1 that has accepted the reception, and the result of the questionnaire to the user performed via the output unit of the reception terminal 1, and transmits these pieces of information to the server 3. Thereafter, the user static data recognition unit 3*a*2 acquires, of the information transmitted to the server 3, information that may affect the determination of the guidance route, and recognizes the information as the user static data.

As the information that may affect the determination of the guidance route in this processing, for example, in addition to essential items such as a destination P1 and a desired arrival time (for example, flight time), there may be mentioned information on attributes of the user, and a course that the user has passed through to reach the guidance area (a store or the like that the user has dropped in before arriving at the airport serving as the guidance area).

Furthermore, as the attributes of the user in this processing, there may be mentioned attributes that may affect the determination of the guidance route. For example, there may be mentioned age, gender, a past airport use history (a guidance route guided in the past), and presence or absence of baggage that needs to be checked in.

Next, the environmental static data recognition unit 3*a*4 of the data recognition unit 3*a* of the server 3 recognizes the environmental static data on the entire guidance area (STEP 102 in FIG. 7).

Specifically, the environmental static data recognition unit 3*a*4 acquires, from the map storage unit 3*e* of the server 3, information that may affect the determination of the guidance route, and recognizes the information as the environmental static data.

As the information that may affect the determination of the guidance route in this processing, in addition to the map information on the guidance area (for example, a position of the reception terminal 1 that has accepted the reception (that is, the guidance start location P0)), there may be mentioned information on facilities such as a toilet and a store that are installed in the guidance area, information on an event being held in the guidance area and construction taking place continuously, and the like.

Next, the route determination unit 3*f*1 of the guidance action determination unit 3*f* of the server 3 determines a reference first route R1, based on the recognized user static data and environmental static data (STEP 103 in FIG. 7).

In the present embodiment, of routes that are from the guidance start location P0 to the destination P1 and through which the user can arrive by the desired arrival time, a route estimated to allow the user to move in the shortest time is the first route R1.

Next, the user dynamic data recognition unit 3*a*1 of the data recognition unit 3*a* of the server 3 recognizes the user dynamic data before the start of the guidance (STEP 104 in FIG. 7).

Specifically, the reception terminal 1 first transmits to the server 3 data on an image of the user captured by the first camera 1*e* of the reception terminal 1 at the time of the user offering the reception via the reception terminal 1, and data on a voice of the user acquired by the first microphone 1c. Thereafter, the user dynamic data recognition unit 3a1 recognizes, as the user dynamic data, a behavior of the user at the start of the guidance, biological information (for example, a physical condition, a degree of fatigue), and the like, based on the transmitted information received by the server 3.

Next, the guidance request estimation unit 3c of the server 3 recognizes the request estimation data based on the user static data (STEP 105 in FIG. 7).

Specifically, the guidance request estimation unit 3c first recognizes, of the user static data recognized by the user static data recognition unit 3a2, data indicating the attribute of the user who desires the guidance. Thereafter, the guidance request estimation unit 3c acquires from the request estimation data storage unit 3d the request estimation data associated with an attribute same as or relating to the attribute.

Next, the guidance request estimation unit 3c estimates the guidance request of the user, based on the recognized user dynamic data, user static data, and request estimation data (STEP 106 in FIG. 7).

Specifically, the guidance request estimation unit 3c first estimates the guidance request of the user (for example, whether the user wants to go to a toilet, whether the user wants to take a break), based on the behavior of the user and the biological information (for example, a physical condition, a degree of fatigue) in the user dynamic data, and the course that the user has passed through to reach the guidance area (for example, whether the user has dropped in a restaurant) in the user static data.

Thereafter, the guidance request estimation unit 3c refers to the request estimation data in which the user dynamic data same as or similar to the recognized user dynamic data is included, and determines whether the guidance request corresponding to the request estimation data and the guidance request estimated this time coincide with each other.

Then, when it is determined that the guidance requests coincide with each other, the guidance request estimation unit 3c establishes the estimated guidance request as the guidance request of the user. On the other hand, when it is determined that the guidance requests do not coincide with each other, the guidance request estimation unit 3c refers to the other user dynamic data and request estimation data and estimates the guidance request of the user again.

Next, the route determination unit 3f1 recognizes the priority from the priority storage unit 3g based on the estimated guidance request (STEP 107 in FIG. 7).

Specifically, the route determination unit 3f1 acquires from the priority storage unit 3g the priority of a facility estimated to be a facility that the user desires to use.

Next, the route determination unit 3f1 recognizes the map information from the map storage unit 3e based on the estimated guidance request (STEP 108 in FIG. 7).

Specifically, the route determination unit 3f1 acquires from the map storage unit 3e average time of use of the facility estimated to be the facility that the user desires to use.

Last, the route determination unit 3f1 modifies the reference first route R1 based on the estimated guidance request and the recognized priority and map information, determines a second route R2 being the guidance route at the start of the guidance, and ends this processing (STEP 109 in FIG. 7).

Specifically, for example, when it is estimated that the user is requesting to use a toilet, the route determination unit 3f1, in consideration of average time of use of a toilet, first searches for, of routes through which the user reaches the destination P1 from the guidance start location P0 by the desired arrival time, a plurality of routes that allow the user to pass through any of toilets.

Thereafter, the route determination unit 3f1 determines, of the plurality of searched routes, a route passing through a toilet with highest priority (for example, a toilet that is least likely to be congested) as the second route R2 being the guidance route at the start of the guidance.

Next, the processing that the server 3 of the guidance system S performs when changing the guidance route during the guidance will be described.

In this processing, the user dynamic data recognition unit 3a1 of the data recognition unit 3a of the server 3 first recognizes current user dynamic data (STEP 201 in FIG. 9).

Specifically, the robot 2 first transmits to the server 3 data on an image of the user captured by the second camera 22d of the robot 2, and data on a voice of the user acquired by the second microphone 22b. Thereafter, the user dynamic data recognition unit 3a1 recognizes, as the current user dynamic data, a behavior of the user during the guidance (for example, an expression, movement of the line of sight), biological information (for example, a physical condition, a degree of fatigue), and the like, based on the information transmitted to the server 3.

Next, the user dynamic data recognition unit 3a1 determines whether the recognized user dynamic data is predetermined user dynamic data set in advance (STEP 202 in FIG. 9).

Some of the actions of the user with respect to the guidance request (that is, the user dynamic data) can be generalized. For example, in the case where the user is concerned about arrival time, the user frequently checks a watch, and in the case where the user wants to use a toilet, the user checks a guidance table indicating a position of a toilet.

Thus, in the guidance system S, the user dynamic data that should be used as a trigger of the change of the guidance content is set in advance, and only when the recognized user dynamic data corresponds to the predetermined user dynamic data set in advance, the subsequent processing for changing the guidance content is executed. As a result, in the guidance system S, excessive execution of the processing is suppressed, so that excessive change of the guidance content and excessive notification associated therewith are suppressed.

As the predetermined user dynamic data, for example, there may be mentioned information indicating that the line of sight of the user has moved to look for something or is focusing on some point, information indicating that the movement direction or movement speed of the user is changed, and information indicating that the user has uttered a voice to convey a request (for example, the user wants to drop in somewhere).

When it is determined that it is not the predetermined user dynamic data (in the case of NO in STEP 202 in FIG. 9), the processing returns to STEP 201, and the user dynamic data recognition unit 3a1 recognizes the user dynamic data again.

On the other hand, when it is determined that it is the predetermined user dynamic data (in the case of YES in STEP 202 in FIG. 9), the environmental dynamic data recognition unit 3a3 of the data recognition unit 3a of the server 3 recognizes the environmental dynamic data on the current location of the robot 2 (consequently, a current location P2 of the user) (STEP 203 in FIG. 9).

Specifically, the robot 2 first transmits to the server 3 data on an image of the vicinity of the user captured by the second camera 22d of the robot 2, and data on a sound in the vicinity of the user acquired by the second microphone 22b. Thereafter, the environmental dynamic data recognition unit 3a3 acquires, of the information transmitted to the server 3, information that may affect the change of the guidance route, and recognizes the information as the environmental dynamic data.

As the information that may affect the change of the guidance route in this processing, for example, there may be mentioned a degree of congestion in the vicinity of the user during the guidance, unscheduled construction, and an event such as a sudden accident.

Next, the environmental static data recognition unit 3a4 of the data recognition unit 3a of the server 3 recognizes the environmental static data on the current location P2 of the user (STEP 204 in FIG. 9).

Specifically, the environmental static data recognition unit 3a4 acquires, from the map storage unit 3e of the server 3, information that may affect the change of the guidance route, and recognizes the information as the environmental static data.

As the information that may affect the change of the guidance route in this processing, there may be mentioned information on facilities such as a toilet and a store that are installed in the vicinity of the current location P2 of the user, information on an event being held in the vicinity of the current location P2 (in the present embodiment, an event being held in an event venue P3) and construction taking place continuously, and the like.

Next, the guidance request estimation unit 3c of the server 3 recognizes the request estimation data based on the recognized user static data (STEP 205 in FIG. 9).

Specifically, similarly to the processing in STEP 105 in FIG. 7, the guidance request estimation unit 3c, based on the data indicating the attribute of the user recognized from the user static data recognized before the start of the guidance (the user static data recognized in STEP 101 in FIG. 7), acquires from the request estimation data storage unit 3d the request estimation data associated with an attribute same as or relating to the attribute.

Next, the guidance request estimation unit 3c estimates the guidance request of the user at the current time point, based on the recognized user dynamic data, environmental dynamic data, environmental static data, and request estimation data (STEP 206 in FIG. 9).

Specifically, the guidance request estimation unit 3c first estimates the guidance request of the user (for example, the user wants to move smoothly because it is congested, the user is interested in a content of an event), based on the user dynamic data (an expression, movement of the line of sight, and the like), the environmental dynamic data (a degree of congestion of the current location P2, and the like), and the environmental static data (an event being held in the event venue P3, and the like).

Thereafter, similarly to the processing in STEP 106 in FIG. 7, the guidance request estimation unit 3c refers to the request estimation data, and establishes the estimated guidance request as the guidance request of the user or estimates the guidance request of the user again.

Next, the route determination unit 3f1 recognizes the priority from the priority storage unit 3g based on the estimated guidance request (STEP 207 in FIG. 9).

Specifically, the route determination unit 3f1 acquires from the priority storage unit 3g the priority of a facility estimated to be a facility that the user desires to use.

Next, the route determination unit 3f1 recognizes the map information relating to the guidance request, based on the estimated guidance request (STEP 208 in FIG. 9).

Specifically, for example, the route determination unit 3f1 acquires from the map storage unit 3e a distance and required time from the current location to a store P4 where a product relating to the event being held in the event venue P3 is handled, average time of use of the store P4, and the like.

Next, the route determination unit 3f1 determines a content of the change of the guidance route, based on the estimated guidance request and the recognized priority and map information (STEP 209 in FIG. 9).

Specifically, for example, when it is estimated that the user is interested in the event being held in the event venue P3 (consequently, the user is requesting to purchase the product relating to the event), the mute determination unit 3f1, in consideration of average time of use of the store handling the product, first searches for, of mutes from the current location P2 to the destination P1, a plurality of routes passing through any of the stores.

Thereafter, the route determination unit 3f1 replaces, of the reference first route R1, a portion from the current location P2 to the destination P1 with, of the plurality of searched routes, a route passing through a store with highest priority (for example, the nearest store P4), and determines the route as a third mute R3 (a content of the change) being the changed guidance mute.

Next, the route determination unit 3f1 recognizes arrival time in the case where the guidance route is changed from the second route R2 to the third mute R3 (STEP 210 in FIG. 10).

Specifically, the mute determination unit 3f1 first calculates an average movement speed from the guidance start location P0 to the current location P2. Thereafter, the route determination unit 3f1 calculates the arrival time based on the average movement speed, the distance from the current location P2 to the destination P1, the average time of use of the store P4, and the current time.

Next, the route determination unit 3f1 determines whether the arrival time in the case where the guidance route is changed is before the desired arrival time of the user (STEP 211 in FIG. 10).

When it is determined that it is not before the desired arrival time (in the case of NO in STEP 211 in FIG. 10), the server 3 ends this processing without performing the subsequent processing.

On the other hand, when it is determined that it is before the desired arrival time (in the case of YES in STEP 211 in FIG. 10), the route determination unit 3f1 recognizes the evaluation data from the evaluation data storage unit 3l based on the recognized user static data (STEP 212 in FIG. 10).

Specifically, the route determination unit 3f1 first recognizes, of the user static data recognized by the user static data recognition unit 3a2, data indicating the attribute of the user. Thereafter, the route determination unit 3f1 acquires from the evaluation data storage unit 3l the evaluation data associated with an attribute same as or relating to the attribute.

Next, the route determination unit 3f1, based on the evaluation data, recognizes a change in the emotion of the user that is predicted in the case where the guidance route is changed (STEP 213 in FIG. 10).

Specifically, the mute determination unit 3f1 first searches for, of the recognized evaluation data, the evaluation data associated with a motion same as or relating to the motion of the robot 2 for this guidance request (for example, the change of the guidance mute itself). Thereafter, the mute determination unit 3f1 recognizes the change in the emotion included in the recognized evaluation data.

Next, the route determination unit 3f1 determines whether the predicted emotional change is positive (STEP 214 in FIG. 10).

When it is determined that it is not positive (in the case of NO in STEP 214 in FIG. 10), the server 3 ends this processing without performing the subsequent processing.

On the other hand, when it is determined that it is positive (in the case of YES in STEP 214 in FIG. 10), the notification instruction unit 3h of the server 3 instructs the robot 2 to notify of the content of the change (STEP 215 in FIG. 10).

Specifically, for example, in the case of processing relating to the change of the guidance route, the notification instruction unit 3h first instructs the robot 2 to notify of information on the change of the guidance mute such as the fact that the product relating to the event being held in the event venue P3 is handled at the store P4, the guidance mute for passing through the store P4 (that is, the third route R3), the arrival time in the case where the guidance mute is changed, and a change in the required time before and after the change, and inquiry information for inquiring about necessity of the change of the guidance route.

Thereafter, the robot 2 that has received this instruction performs the notification via the second touch panel 22a and the second speaker 22c that serve as the output unit.

Next, the user dynamic data recognition unit 3a1 recognizes the user dynamic data after the notification of the inquiry information (STEP 216 in FIG. 10).

Specifically, the robot 2 first transmits to the server 3 data on an image of the user captured by the second camera 22d of the robot 2 and data on a voice of the user acquired by the second microphone 22b after the notification of the inquiry information. Thereafter, the user dynamic data recognition unit 3a1 recognizes the behavior of the user and the like as the user dynamic data, based on the information transmitted to the server 3.

Next, the reaction recognition unit 3i of the server 3 recognizes a reaction of the user, based on the user dynamic data recognized after the notification of the inquiry information (STEP 217 in FIG. 10).

Specifically, for example, the system designer of the guidance system S or the like sets in advance a behavior in which the user may be estimated to have indicated a permission, and a behavior in which the user may be estimated to have indicated a refusal, and the reaction recognition unit 3i recognizes the reaction of the user (specifically, whether the change of the guidance route is permitted), depending on which of the behaviors the user dynamic data recognized after the notification corresponds to.

Next, the route determination unit 3f1 determines whether the reaction recognized by the reaction recognition unit 3i is a reaction that permits the change of the guidance route (STEP 218 in FIG. 10).

When it is determined that it is not a reaction that permits the change of the guidance route (in the case of NO in STEP 218 in FIG. 10), the server 3 ends this processing without performing the subsequent processing.

On the other hand, when it is determined that it is a reaction that permits the change of the guidance route (in the case of YES in STEP 218 in FIG. 10), the route determination unit 3f1 establishes the change of the guidance route, and the robot control unit 3j of the server 3 issues to the robot 2 an instruction for the guidance action according to the changed guidance route (STEP 219 in FIG. 10).

Specifically, the robot control unit 3j transmits to the robot 2 an instruction for guiding the user along the third route R3 being the changed guidance route.

Last, the guidance request estimation unit 3c associates, with the estimated guidance request, the user dynamic data used at the time of the estimation of this guidance request (that is, the user dynamic data recognized in STEP 201 in FIG. 9) and the user static data, stores them in the request estimation data storage unit 3d, and ends this processing (STEP 220 in FIG. 10).

In the server 3 configured as described above, during the guidance (specifically, during the period from the start of the guidance to the end of the guidance), the guidance route is changed based on the estimated guidance request of the user. That is, the guidance route is changed based on not only a request clearly expressed by the user but also a request that the user potentially has.

As a result, the guidance route becomes suitable for the guidance request of the user. For example, a facility that the user needs to use (for example, a break room, a toilet), and a position of a store where goods and services of interest to the user are provided are taken into consideration.

Thus, according to the guidance system S comprising this server 3 and the guide robot control method using the same, the guidance route corresponds to the guidance request of the user, and the change of the guidance route is performed while respecting the user's intention, so that the user can receive the guidance with less stress.

In the processing for the change of the guidance route in the present embodiment, the user dynamic data is detected sequentially, and the guidance request is accordingly estimated again to perform the change of the guidance route. This is to sequentially grasp the guidance request of the user that changes from moment to moment so as to suitably change the guidance route.

However, the present invention is not limited to such a configuration. For example, the recognition of the user dynamic data, the estimation of the guidance request, and consequently the change of the guidance route may be performed only at a predetermined timing (for example, a timing of passing through a predetermined location, a timing at which a predetermined time elapses).

Furthermore, for example, the recognition of the user dynamic data, the estimation of the guidance request, and consequently the change of the guidance mute may be performed only when, instead of the user dynamic data, the environmental dynamic data is recognized sequentially and predetermined environmental dynamic data is recognized (for example, when the degree of congestion becomes equal to or higher than a predetermined degree).

Furthermore, in the present embodiment, when it is determined that the arrival time in the case where the guidance mute is changed is not before the desired arrival time (in the case of NO in STEP 211 in FIG. 10), when it is determined that the predicted emotional change is not positive (in the case of NO in STEP 214 in FIG. 10), and when it is determined that the reaction after the notification is not a reaction indicating a permission (in the case of NO in STEP 218 in FIG. 10), the server 3 ends the processing without performing the subsequent processing. This is to give priority to guiding the user to the destination at the desired arrival time, and to give priority to a direct desire of the user.

However, the present invention is not limited to such a configuration. For example, when the recognized user dynamic data includes a direct instruction (for example, when the user instructs the robot to lead to a predetermined store), when the recognized environmental dynamic data has a high degree of urgency (when an accident requiring evacuation occurs near the current location), or the like, the change of the guidance route may be executed without performing the determination on the arrival time and the determination on the emotional change.

Furthermore, in the present embodiment, the determination of the guidance route at the start of the guidance and the change of the content of the guidance route are performed based on a physiological desire of the user or a display that has attracted the interest of the user during the guidance.

However, the present invention is not limited to such a configuration. For example, at the time of the determination and change of the guidance route, of the user static data, a past facility use history of the user may be referred to, and a route passing through the facility used in the past may be added as a candidate. Furthermore, of the user static data, an attribute of the user (for example, clothes, a brand of a carried item) may be referred to, and a route passing through a store corresponding to the attribute (for example, a store relating to the recognized brand) or the like may be added as a candidate.

Furthermore, for example, of the environmental static data, a time zone (specifically, whether it is a time zone to eat) may be recognized, and according to the time zone, a route passing through an eating establishment may be added as a candidate. Furthermore, of the environmental static data, remaining time until the desired arrival time may be recognized, and according to the remaining time, whether to give priority to a passage that is easily passable (for example, wide and large) or whether to give priority to a passage with a shorter required time may be referred to at the time of the determination and change of the guidance route.

Furthermore, for example, when it is estimated based on the user dynamic data and the environmental dynamic data during the guidance that the user has an unpleasant feeling about the surrounding situation (for example, a degree of congestion), the guidance route may be changed to a route with a low degree of congestion such that the user can move smoothly.

Furthermore, for example, a general tendency such as a route with which the user is generally highly satisfied or a route avoiding a place where the guidance speed highly likely needs to be adjusted due to fatigue may be recognized based on, in the previous or earlier guidance, the user static data, the evaluation data, and the like, and the determination and change of the guidance route may be performed by referring to the tendency.

Next, processing that the guidance system S performs when determining the guidance speed at the start of the guidance and processing that the guidance system S performs when changing the guidance speed during the guidance will be described with reference to FIGS. 5, 8, and 11 to 13.

Figure 11:
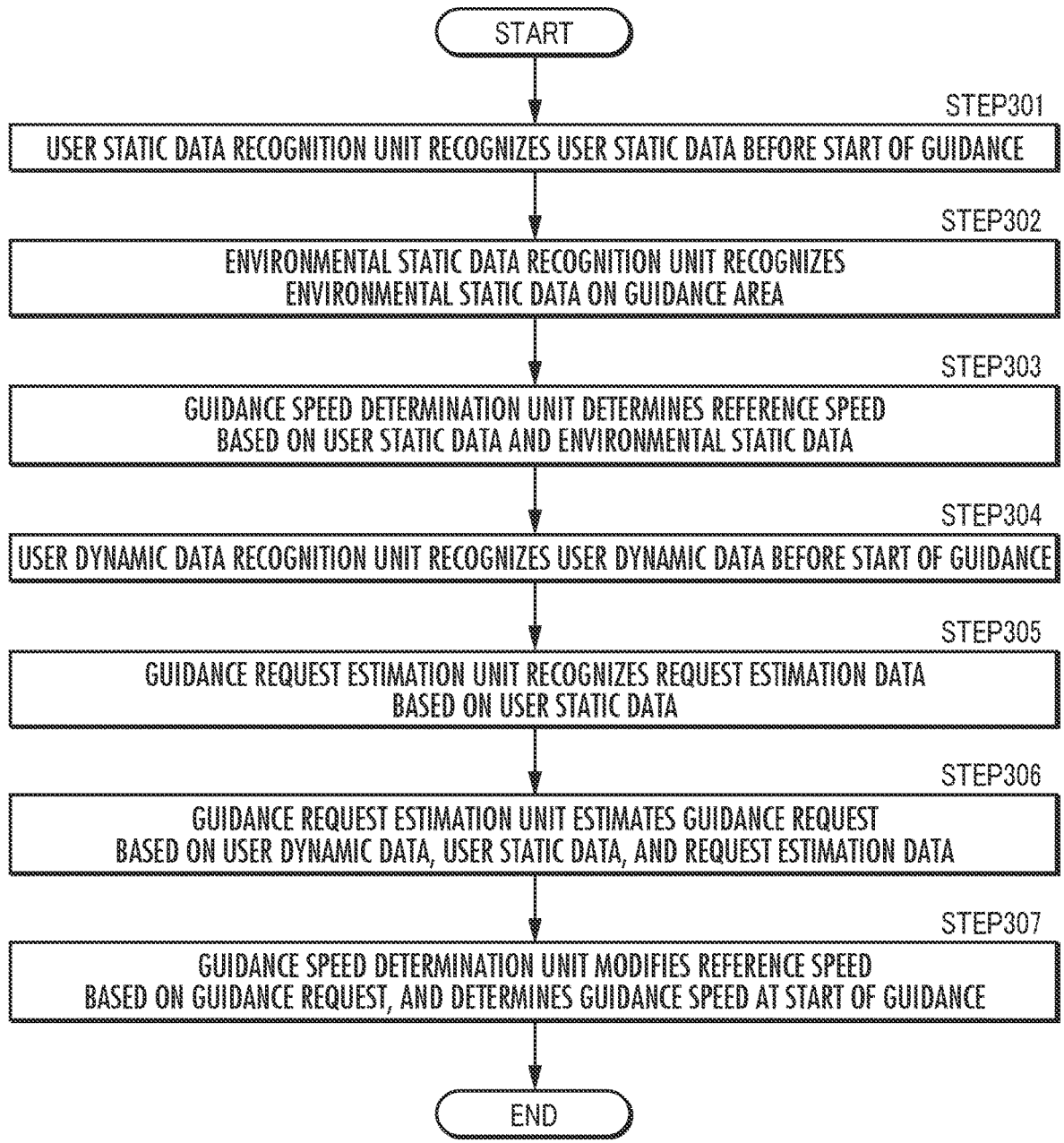
FIG. 11 is a flowchart illustrating processing that the guidance system of FIG. 1 performs when determining a guidance speed at start of guidance.
Figure 12:
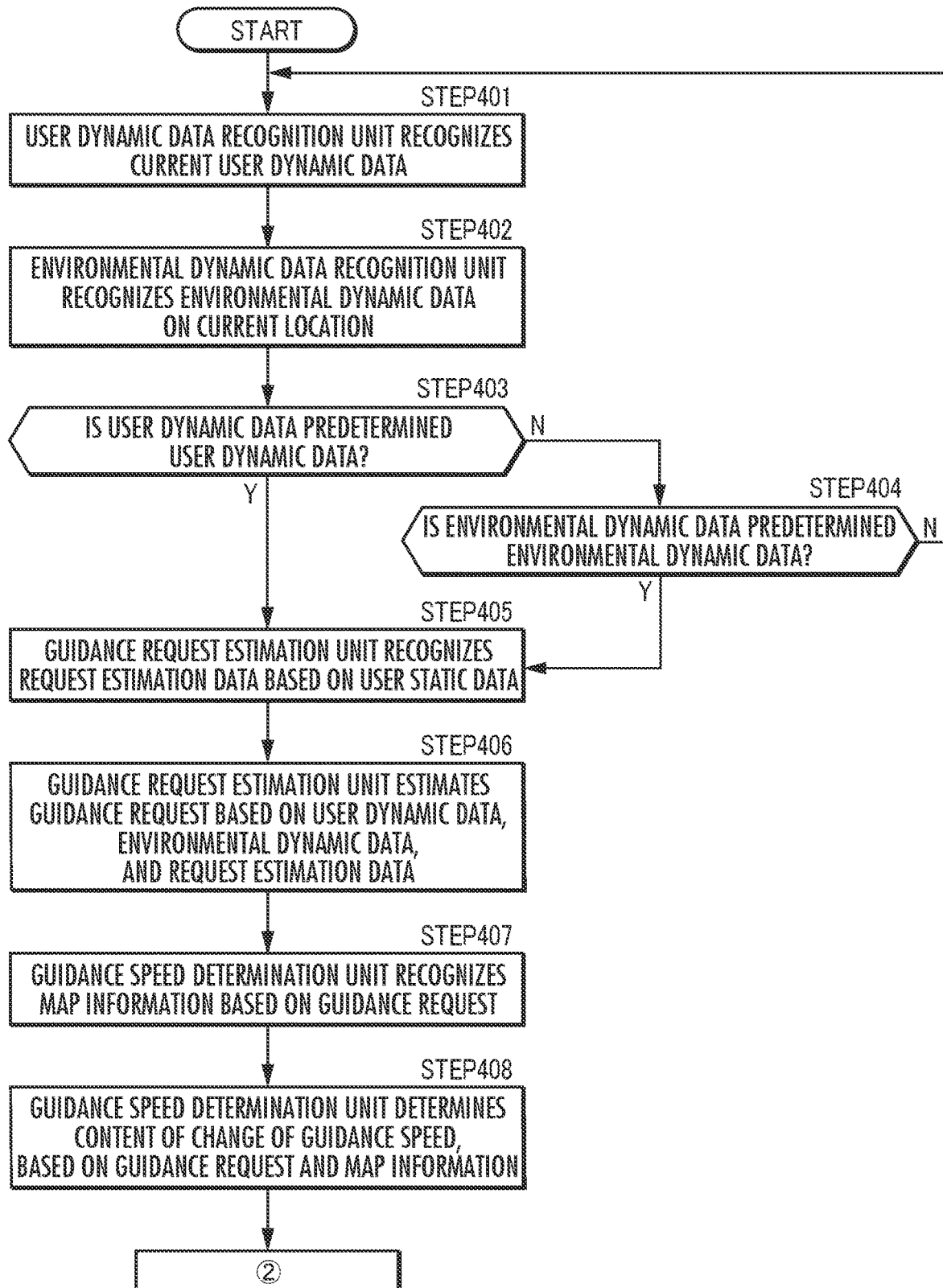
FIG. 12 is a flowchart illustrating, of processing that the guidance system of FIG. 1 performs when changing a guidance speed during guidance, processing until a content of the change of the guidance speed is determined.
Figure 13:
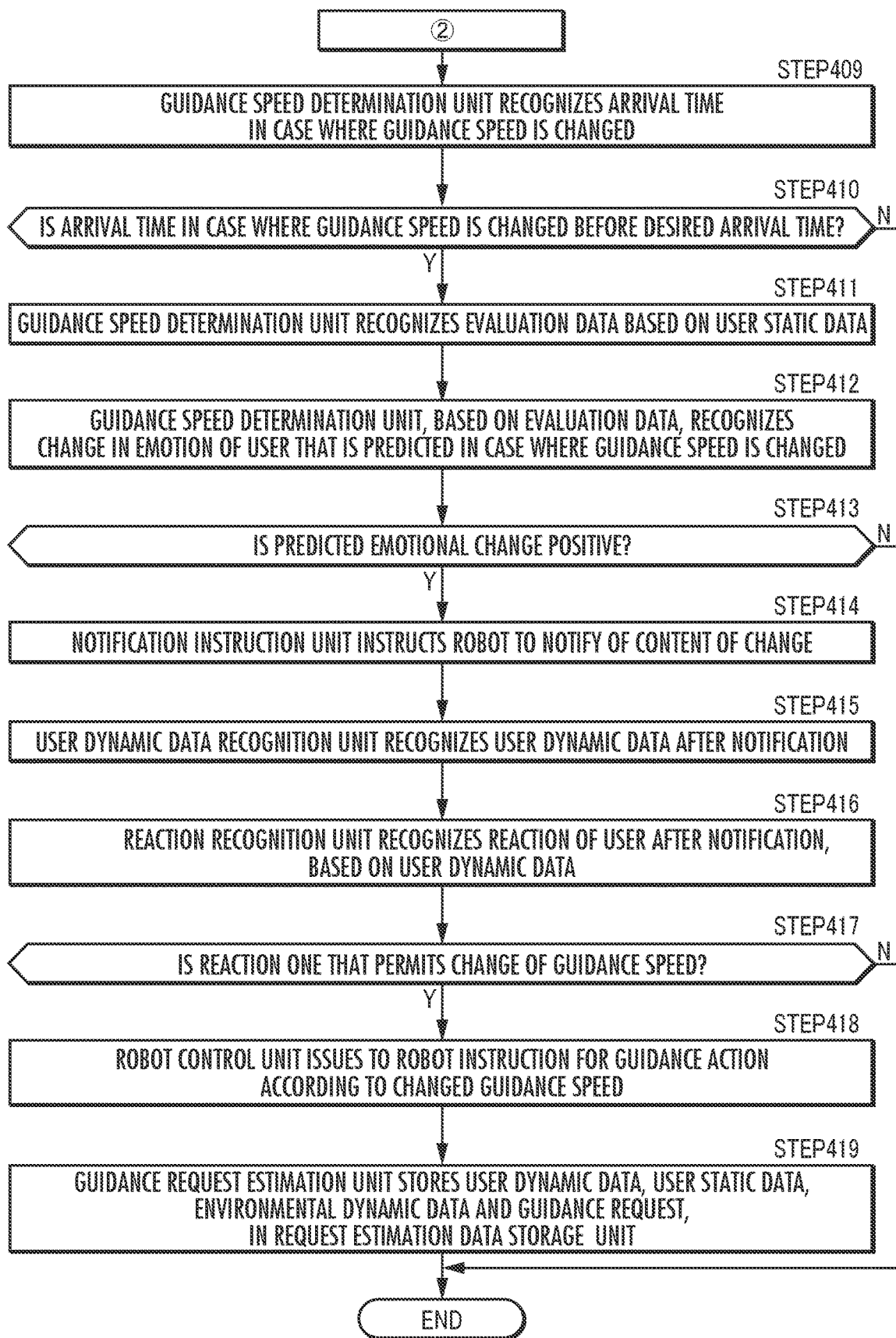
FIG. 13 is a flowchart illustrating, of the processing that the guidance system of FIG. 1 performs when changing a guidance speed during guidance, processing until the change of the guidance speed is executed.

FIG. 11 is a flowchart illustrating the processing that the server 3 of the guidance system S performs when determining the guidance speed at the start of the guidance. Furthermore, FIG. 12 is a flowchart illustrating, of the processing that the server 3 of the guidance system S performs when changing the guidance speed during the guidance, processing until a content of the change of the guidance speed is determined. Furthermore, FIG. 13 is a flowchart illustrating, of the processing that the server 3 of the guidance system S performs when changing the guidance speed during the guidance, processing until the change of the guidance speed is executed.

First, the processing that the guidance system S performs when determining the guidance speed at the start of the guidance will be described.

In this processing, the user static data recognition unit 3a2 of the data recognition unit 3a of the server 3 first recognizes the user static data before the start of the guidance (STEP 301 in FIG. 11).

Specifically, similarly to the processing in STEP 101 in FIG. 7, the reception terminal 1 first recognizes information input by the user at the time of reception, information on the reception terminal 1 that has accepted the reception, and the result of the questionnaire to the user performed via the output unit of the reception terminal 1, and transmits these pieces of information to the server 3.

Thereafter, the user static data recognition unit 3a2 acquires, the information transmitted from the reception terminal 1, information that may affect the determination of the guidance speed, and recognizes the information as the user static data.

Figure 8:
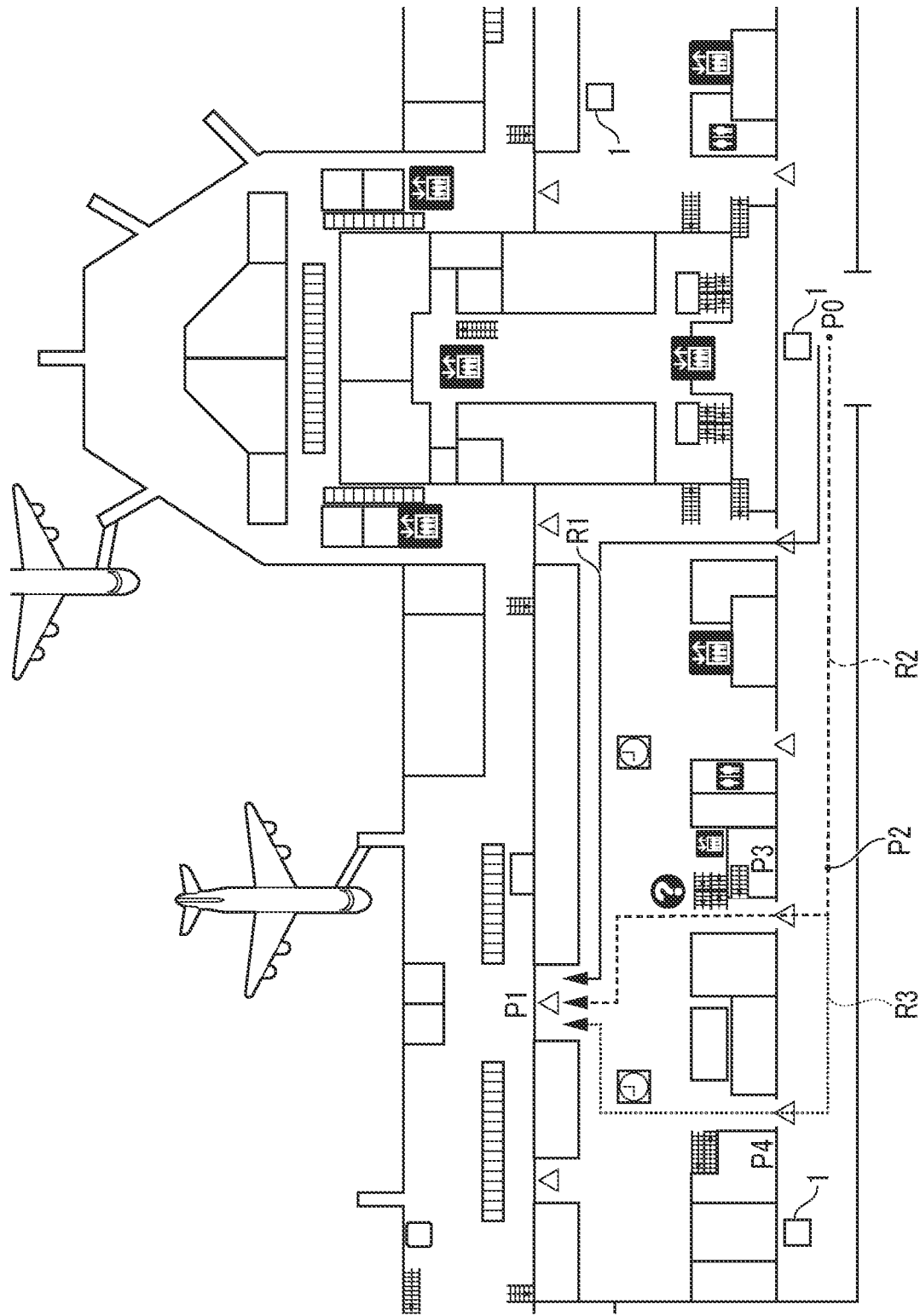
FIG. 8 is a schematic view illustrating a map of an airport where the user is guided by the guidance system of FIG. 1.

As the information that may affect the determination of the guidance speed in this processing, for example, in addition to essential items such as a position of the reception terminal 1 that has accepted the reception (that is, the guidance start location P0 in FIG. 8), the destination P1 in FIG. 8, and a desired arrival time (for example, flight time), there may be mentioned information on attributes of the user, and a course that the user has passed through to reach the guidance area (a store or the like that the user has dropped in before arriving at the airport serving as the guidance area).

Furthermore, as the attributes of the user in this processing, there may be mentioned attributes that may affect the determination of the guidance speed. For example, there may be mentioned age, gender, presence or absence of physical disability, use or non-use of a wheelchair, presence or absence of companion, and pregnancy status.

Next, the environmental static data recognition unit 3a4 of the data recognition unit 3a of the server 3 recognizes the environmental static data on the entire guidance area (STEP 302 in FIG. 11).

Specifically, the environmental static data recognition unit 3a4 acquires, from the map storage unit 3e of the server 3, information that may affect the determination of the guidance speed, and recognizes these pieces of information as the environmental static data.

As the information that may affect the determination of the guidance speed in this processing, in addition to the map information on the guidance area, there may be mentioned information on an event being held in the guidance area and construction taking place continuously (consequently, information on a place where congestion is predicted), and the like.

Next, the guidance speed determination unit 3f2 of the guidance action determination unit 3f of the server 3 determines a reference first speed based on the recognized user static data and environmental static data (STEP 303 in FIG. 11).

In the present embodiment, as illustrated in FIG. 8, of routes that are from the guidance start location P0 to the destination P1 and through which the user can arrive by the desired arrival time, a route estimated to allow the user to move in the shortest time is the first route R1. Then, the guidance speed estimated in the case of moving through the first route R1 is the reference first speed.

Next, the user dynamic data recognition unit 3*a*1 of the data recognition unit 3*a* of the server 3 recognizes the user dynamic data before the start of the guidance (STEP 304 in FIG. 11).

Specifically, similarly to the processing in STEP 104 in FIG. 7, the user dynamic data recognition unit 3*a*1 recognizes, as the user dynamic data, a behavior of the user at the start of the guidance, biological information (for example, a physical condition, a degree of fatigue), and the like, based on the information transmitted from the reception terminal 1.

Next, the guidance request estimation unit 3*c* of the server 3 recognizes the request estimation data based on the user static data (STEP 305 in FIG. 11).

Specifically, similarly to the processing in STEP 105 in FIG. 7 and STEP 205 in FIG. 9, the guidance request estimation unit 3*c*, based on the data indicating the attribute of the user recognized from the user static data, acquires from the request estimation data storage unit 3*d* the request estimation data associated with an attribute same as or relating to the attribute.

Next, the guidance request estimation unit 3*c* estimates the guidance request of the user, based on the recognized user dynamic data, user static data, and request estimation data (STEP 306 in FIG. 11).

Specifically, the guidance request estimation unit 3*c* first estimates the guidance request of the user (specifically, whether the guidance speed should be faster or slower, or the like), based on the behavior of the user and the biological information (for example, a physical condition, a degree of fatigue) in the user dynamic data, and the course that the user has passed through to reach the guidance area (for example, presence or absence of physical disability) in the user static data.

Thereafter, the guidance request estimation unit 3*c* refers to the request estimation data in which the user dynamic data same as or similar to the recognized user dynamic data is included, and determines whether the guidance request corresponding to the request estimation data and the guidance request estimated this time coincide with each other.

Then, when it is determined that the guidance requests coincide with each other, the guidance request estimation unit 3*c* establishes the estimated guidance request as the guidance request of the user. On the other hand, when it is determined that the guidance requests do not coincide with each other, the guidance request estimation unit 3*c* refers to the other user dynamic data and user estimation data and estimates the guidance request of the user again.

Last, the guidance speed determination unit 3*f*2 modifies the reference first speed based on the estimated guidance request, determines a second speed being the guidance speed at the start of the guidance, and ends this processing (STEP 307 in FIG. 11).

Specifically, the guidance speed determination unit 3*f*2 adjusts the first speed according to the desired guidance speed of the user and determines it as the second speed.

In the case where the period from the current time to the arrival time is short, in the case where the desired guidance speed of the user is extremely late, or the like, the most important purpose of guiding the user to the destination by the desired arrival time may not be achieved depending on movement of the user.

In such a case, processing for examining means to increase the movement speed of the user may be performed. Specifically, for example, without performing the processing for modifying the first speed and determining the second speed, processing for determining whether to use a robot of a ridable type in the guidance and processing for bringing a ridable robot may be performed.

Next, the processing that the server 3 of the guidance system S performs when changing the guidance speed during the guidance will be described.

In this processing, the user dynamic data recognition unit 3*a*1 of the data recognition unit 3*a* of the server 3 first recognizes current user dynamic data (STEP 401 in FIG. 12).

Specifically, similarly to the processing in STEP 201 in FIG. 9, the user dynamic data recognition unit 3*a*1 recognizes, as the current user dynamic data, a behavior of the user during the guidance (for example, an expression, movement of the line of sight), biological information (for example, a physical condition, a degree of fatigue), and the like, based on the information transmitted from the robot 2.

Next, the environmental dynamic data recognition unit 3*a*3 of the data recognition unit 3*a* of the server 3 recognizes the environmental dynamic data on the current location of the robot 2 (consequently, the current location P2 of the user) (STEP 402 in FIG. 12).

Specifically, similarly to the processing in STEP 203 in FIG. 9, the environmental dynamic data recognition unit 3*a*3 acquires, of the information transmitted from the robot 2, information that may affect the change of the guidance speed, and recognizes the information as the environmental dynamic data.

As the information that may affect the change of the guidance speed in this processing, for example, there may be mentioned information on a degree of congestion in the vicinity of the user during the guidance, a magnitude of noise in the vicinity of the user, and a movement speed of the other user.

This is because, for example, in the case where the vicinity of the user is congested, it becomes difficult for the user to move, and thus the guidance speed needs to be reduced.

Furthermore, this is because, for example, in the case where the magnitude of surrounding noise is large, it is desired to pass through such a noisy area as soon as possible, and thus the guidance speed needs to be increased.

Furthermore, this is because, for example, in the case where the movement speed of the other user significantly differs from the current guidance speed, there is a risk of collision, and thus it is necessary to bring the guidance speed closer to the movement speed to some extent. Next, the user dynamic data recognition unit 3*a*1 determines whether the recognized user dynamic data is predetermined user dynamic data set in advance (STEP 403 in FIG. 12).

Specifically, similarly to the processing in STEP 202 in FIG. 9, the system designer or the like sets in advance the user dynamic data that should be used as a trigger of the change of the guidance content, and the user dynamic data recognition unit 3*a*1 determines whether the recognized user dynamic data corresponds to the predetermined user dynamic data set in advance.

As the predetermined user dynamic data, for example, there may be mentioned information indicating that the line of sight of the user has moved to look for something or is focusing on some point, information indicating that the movement direction or movement speed of the user is changed, and information indicating that the user has uttered a voice that conveys a request (for example, want to move faster).

When it is determined that it is not the predetermined user dynamic data (in the case of NO in STEP 403 in FIG. 12), the environmental dynamic data recognition unit 3*a*3 determines whether the recognized environmental dynamic data is predetermined environmental dynamic data set in advance (STEP 404 in FIG. 12).

Some of the environmental dynamic data can be generalized as to how it affects the guidance request of the user. For example, in the case where the degree of congestion becomes high, it becomes difficult for the user to move, and thus the guidance request for reducing the guidance speed occurs.

Thus, in the guidance system S, the environmental dynamic data that should be used as a trigger of the change of the guidance content is set in advance, and only when the recognized environmental dynamic data corresponds to the predetermined environmental dynamic data set in advance, the subsequent processing for changing the guidance content is executed. As a result, in the guidance system S, excessive execution of the processing is suppressed, so that excessive change of the guidance content and excessive notification associated therewith are suppressed.

As the environmental dynamic data that should be used as a trigger of the change of the guidance content, for example, there may be mentioned information indicating that the degree of congestion has risen, information indicating that the magnitude of noise in the vicinity of the user has increased, and information indicating that a difference between the movement speed of the user during the guidance and the movement speed of the other user has become equal to or more than a predetermined value.

When it is determined that it is not the predetermined environmental dynamic data (in the case of NO in STEP 404 in FIG. 12), the server 3 executes the processing of STEPs 401 to 404 again.

On the other hand, when it is determined that it is the predetermined user dynamic data (in the case of YES in STEP 403 in FIG. 12), or when it is determined that it is the predetermined environmental dynamic data (in the case of YES in STEP 404 in FIG. 12), the guidance request estimation unit 3c of the server 3 recognizes the request estimation data based on the recognized user static data (STEP 405 in FIG. 12).

Specifically, similarly to the processing in STEP 105 in FIG. 7. STEP 205 in FIG. 9, and STEP 305 in FIG. 11, the guidance request estimation unit 3c, based on the data indicating the attribute of the user recognized from the user static data recognized before the start of the guidance (the user static data recognized in STEP 301 in FIG. 11), acquires from the request estimation data storage unit 3d the request estimation data associated with an attribute same as or relating to the attribute.

Next, the guidance request estimation unit 3c estimates the guidance request of the user at the current time point, based on the recognized user dynamic data, environmental dynamic data, and request estimation data (STEP 406 in FIG. 12).

Specifically, the guidance request estimation unit 3c, based on the user dynamic data (an expression, movement of the line of sight, and the like) and the environmental dynamic data (a degree of congestion of the current location, and the like), first estimates the guidance request of the user (for example, it is difficult to follow the robot because the degree of congestion is high, the user is interested in a content of an event and thus wants to move while watching the atmosphere once).

Thereafter, similarly to the processing in STEP 106 in FIG. 7. STEP 206 in FIG. 9, and STEP 306 in FIG. 11, the guidance request estimation unit 3c refers to the request estimation data, and establishes the estimated guidance request as the guidance request of the user or estimates the guidance request of the user again.

Next, the guidance speed determination unit 3f2 of the guidance action determination unit 3f of the server 3 recognizes the map information relating to the guidance request, based on the estimated guidance request (STEP 407 in FIG. 12).

Specifically, for example, the guidance speed determination unit 3f2 acquires from the map storage unit 3e a passage or the like that is located near the current guidance route (third route R3) and less likely to be congested.

Next, the guidance speed determination unit 3f2 determines the content of the change of the guidance speed, based on the estimated guidance request, and the recognized priority and map information (STEP 408 in FIG. 12).

Specifically, for example, when the degree of congestion at the current location is high, and it is estimated that the user feels difficulty in following the robot 2, the guidance speed determination unit 3f2 first calculates the guidance speed that makes it easier for the user to follow. Thereafter, the guidance speed determination unit 3f2 determines how and how much the second speed being the current guidance speed should be changed (the content of the change of the guidance speed).

Next, the guidance speed determination unit 3f2 recognizes arrival time in the case where the guidance speed is changed (STEP 409 in FIG. 13).

Specifically, the guidance speed determination unit 3f2 first calculates how much period and distance the change of the guidance speed should be continued to satisfy the estimated guidance request (for example, whether it is possible to finish passing through an area with a high degree of congestion). Thereafter, the guidance speed determination unit 3f2 calculates the arrival time based on the calculated period and distance that should be continued, the current time, and the distance from the current location to the destination.

Next, the guidance speed determination unit 3f2 determines whether the arrival time in the case where the guidance speed is changed is before the desired arrival time of the user (STEP 410 in FIG. 13).

When it is determined that it is not before the desired arrival time (in the case of NO in STEP 410 in FIG. 13), the server 3 ends this processing without performing the subsequent processing.

On the other hand, when it is determined that it is before the desired arrival time (in the case of YES in STEP 410 in FIG. 13), the guidance speed determination unit 3f2 recognizes the evaluation data from the evaluation data storage unit 3l based on the recognized user static data (STEP 411 in FIG. 13).

Specifically, similarly to the processing in STEP 212 in FIG. 10, the guidance speed determination unit 3f2, based on the data indicating the attribute of the user recognized from the user static data recognized before the start of the guidance (the user static data recognized in STEP 301 in FIG. 11), acquires from the evaluation data storage unit 3l the evaluation data associated with an attribute same as or relating to the attribute.

Next, the guidance speed determination unit 3f2, based on the evaluation data, recognizes a change in the emotion of the user that is predicted in the case where the guidance speed is changed (STEP 412 in FIG. 13).

Specifically, similarly to the processing in STEP 213 in FIG. 10, the guidance speed determination unit 3f2, based on a motion of the robot 2 scheduled to be performed for this guidance request (for example, the change of the guidance speed itself), recognizes the evaluation data associated with the motion and recognizes the change in the emotion included in the evaluation data.

Next, the guidance speed determination unit 3f2 determines whether the predicted emotional change is positive (STEP 413 in FIG. 13).

When it is determined that the emotional change is not positive (in the case of NO in STEP 413 in FIG. 13), the server 3 ends this processing without performing the subsequent processing.

On the other hand, when it is determined that it is positive (in the case of YES in STEP 413 in FIG. 13), the notification instruction unit 3h of the server 3 instructs the robot 2 to notify of the content of the change (STEP 414 in FIG. 13).

Specifically, for example, in the case of processing relating to the change of the guidance speed, the notification instruction unit 3h first instructs the robot 2 to notify of information on the change of the guidance speed such as the fact that the guidance speed is to be changed, the period and distance for changing the guidance speed, the reason for changing the guidance speed (that is, the estimated guidance request), the arrival time in the case where the guidance speed is changed, and a change in the required time before and after the change, and inquiry information for inquiring about necessity of the change of the guidance speed.

Thereafter, the robot 2 that has received this instruction performs the notification via the second touch panel 22a and the second speaker 22c that serve as the output unit.

Next, the user dynamic data recognition unit 3a1 recognizes the user dynamic data after the notification of the inquiry information (STEP 415 in FIG. 13).

Specifically, similarly to the processing in STEP 216 in FIG. 9, the user dynamic data recognition unit 3a1 recognizes, as the user dynamic data, a behavior of the user after the notification of the inquiry information, and the like, based on the information transmitted from the robot 2.

Next, the reaction recognition unit 3i of the server 3 recognizes a reaction of the user, based on the user dynamic data recognized after the notification of the inquiry information (STEP 416 in FIG. 13).

Specifically, similarly to the processing in STEP 217 in FIG. 9, for example, the reaction recognition unit 3i recognizes the reaction of the user (specifically, whether the change of the guidance speed is permitted), depending on whether the user dynamic data recognized after the notification corresponds to the behavior set in advance.

Next, the guidance speed determination unit 3f2 determines whether the reaction recognized by the reaction recognition unit 3i is a reaction that permits the change of the guidance speed (STEP 417 in FIG. 13).

When it is determined that it is not a reaction that permits the change of the guidance speed (in the case of NO in STEP 417 in FIG. 13), the server 3 ends this processing without performing the subsequent processing.

On the other hand, when it is determined that it is a reaction that permits the change of the guidance speed (in the case of YES in STEP 417 in FIG. 13), the guidance speed determination unit 3f2 establishes the change of the guidance speed, and the robot control unit 3j of the server 3 issues to the robot 2 an instruction for the guidance action according to the changed guidance speed (STEP 418 in FIG. 13).

Specifically, the robot control unit 3j transmits to the robot 2 an instruction for guiding the user at the changed guidance speed.

Last, the guidance request estimation unit 3c associates, with the estimated guidance request, the user dynamic data used at the time of the estimation of this guidance request (that is, the user dynamic data recognized in STEP 401 in FIG. 12), the environmental dynamic data (that is, the environmental dynamic data recognized in STEP 402 in FIG. 12), and the user static data, stores them in the request estimation data storage unit 3d, and ends this processing (STEP 419 in FIG. 13).

In the server 3 configured as described above, during the guidance (specifically, during the period from the start of the guidance to the end of the guidance), the guidance speed is changed based on the estimated guidance request of the user. That is, the guidance speed is changed based on not only a request clearly expressed by the user but also a request that the user potentially has.

As a result, the guidance speed becomes suitable for the guidance request of the user. For example, a degree of fatigue of the user, discomfort due to congestion, and a position of a facility of interest to the user are taken into consideration.

Thus, according to the guidance system S comprising this server 3 and the guide robot control method using the same, the guidance speed corresponds to the guidance request of the user, and the change of the guidance speed is performed while respecting the user's intention, so that the user can receive the guidance with less stress.

In the processing for the change of the guidance speed in the present embodiment, the user dynamic data is detected sequentially, and the guidance request is accordingly estimated again to perform the change of the guidance speed. This is to sequentially grasp the guidance request of the user that changes from moment to moment so as to suitably change the guidance speed.

However, the present invention is not limited to such a configuration. For example, the recognition of the user dynamic data, the estimation of the guidance request, and consequently the change of the guidance speed may be performed only at a predetermined timing (for example, a timing of passing through a predetermined location, a timing at which a predetermined time elapses).

Furthermore, for example, the recognition of the user dynamic data, the estimation of the guidance request, and consequently the change of the guidance speed may be performed only when, instead of the user dynamic data, the environmental dynamic data is recognized sequentially and predetermined environmental dynamic data is recognized (for example, when the degree of congestion becomes equal to or higher than a predetermined degree).

Furthermore, in the present embodiment, when it is determined that the arrival time in the case where the guidance speed is changed is not before the desired arrival time (in the case of NO in STEP 410 in FIG. 13), when it is determined that the predicted emotional change is not positive (in the case of NO in STEP 414 in FIG. 13), and when it is determined that the reaction after the notification is not a reaction indicating a permission (in the case of NO in STEP 417 in FIG. 13), the server 3 ends the processing without performing the subsequent processing. This is to give priority to guiding the user to the destination at the desired arrival time, and to give priority to a direct desire of the user.

However, the present invention is not limited to such a configuration. For example, when the recognized user dynamic data includes a direct instruction (for example, when the user instructs the robot to lead to a predetermined store), when the recognized environmental dynamic data has a high degree of urgency (when an accident requiring evacuation occurs near the current location), or the like, the change of the guidance speed may be executed without performing the determination on the arrival time and the determination on the emotional change.

Furthermore, in the present embodiment, the change of the guidance speed is performed by using the user dynamic data and the environmental dynamic data as the triggers. However, for example, the change of the guidance speed may be performed based on the user static data and the environmental static data.

For example, when it is estimated from the user static data (information indicating user's clothes, belongings, or the like) that the user is interested in a predetermined brand, the environmental static data may be used to search for a store having an attribute of handling the brand (consequently, a store that the user likely wants to drop in), and the guidance speed may be made slower around the store such that the user can get attracted to the store easily.

Furthermore, in the case of such a configuration, the priority may be set for each store according to the cost paid by the facility to the manager of the guidance area, or the like, and the guidance speed may be made especially slower around a store with high priority such that the user can get attracted to it.

Next, processing that the guidance system S performs when determining the target position immediately after the start of the guidance and processing that the guidance system S performs when changing the target position during the guidance will be described with reference to FIGS. 5 and 14 to 18.

Here, "target position" represents a position serving as a target of the relative position of the robot 2 with respect to the user during the guidance. Furthermore, "relative position" may represent only a distance from the user to the robot or only a direction in which the robot is located with respect to the user and also may represent a degree of a change in the relative position during turning or the like. However, the target position or the relative position in the following description uses a distance from the user to the robot and a direction in which the robot is located with respect to the user.

Furthermore, here. "direction" represents a direction of the robot with respect to the user in a plane parallel to movement surfaces of the user and the robot.

Figure 14:
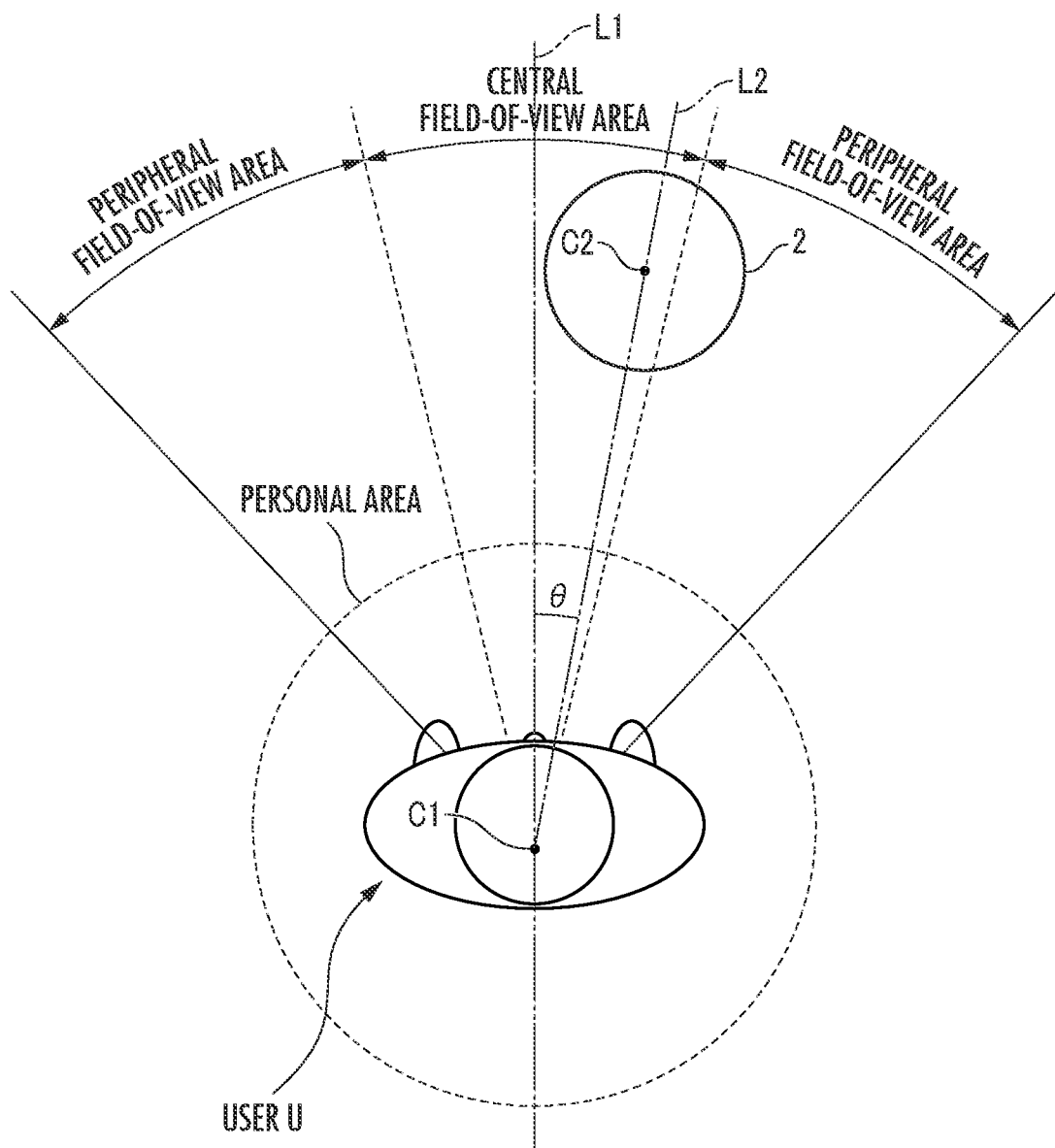
FIG. 14 is a schematic view illustrating an example of a relative position between the user and the robot.

For example, as illustrated in FIG. 14, it represents, in the case where the user and the robot move on level ground, in a plan view, an angle θ formed by a line passing through the center of the body of the user and extending in the front-rear direction (a line included in a sagittal plane, a first virtual line L1), and a line passing through a first center C1 being the center of the body of the user and a second center C2 being the center of the robot 2 (second virtual line L2) (that is, a slope of the second virtual line L2 with respect to the first virtual line L1).

Figure 15:
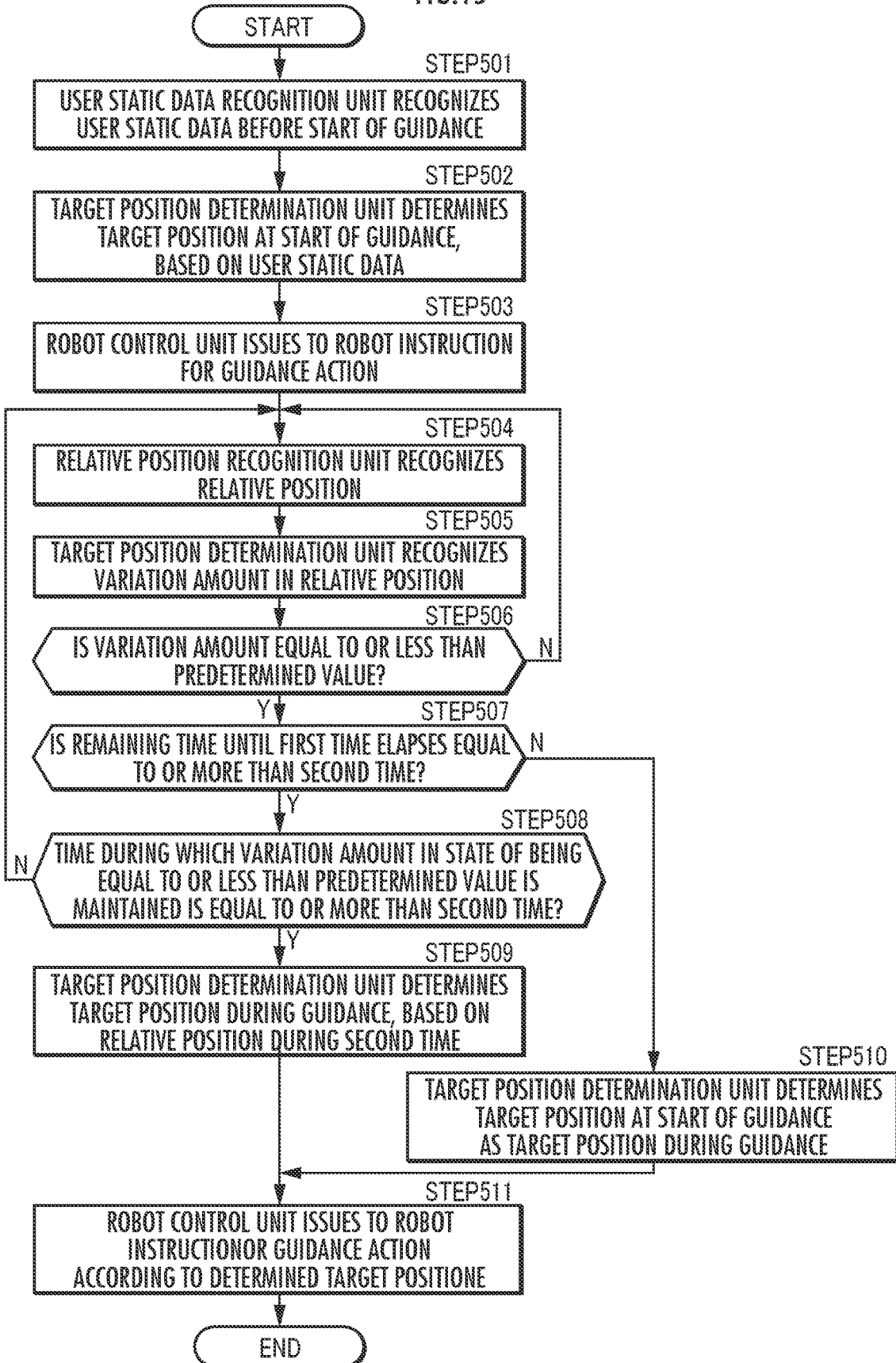
FIG. 15 is a flowchart illustrating processing that the guidance system of FIG. 1 performs when determining a target position immediately after start of guidance.
Figure 17:
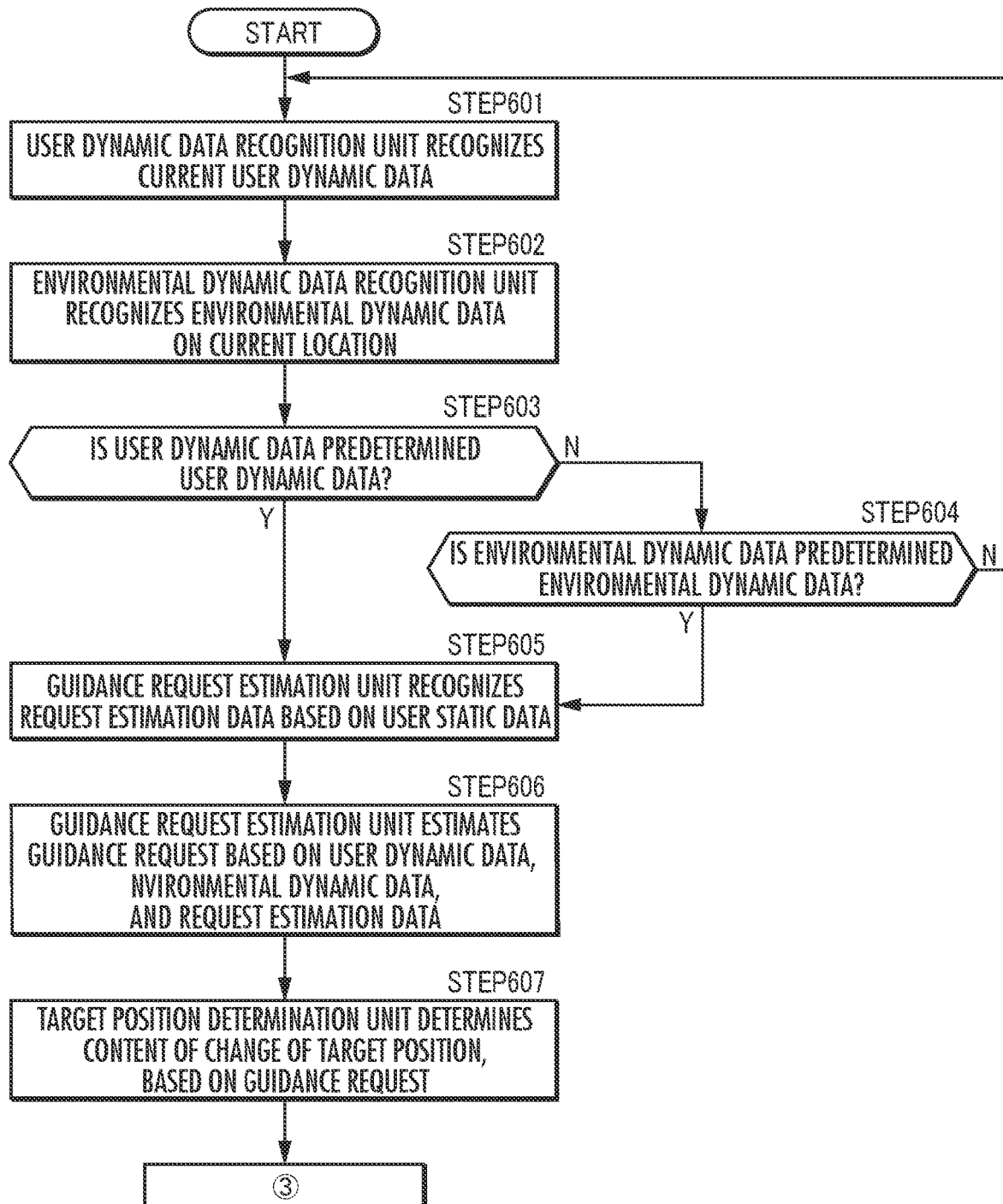
FIG. 17 is a flowchart illustrating, of processing that the guidance system of FIG. 1 performs when changing a target position during guidance, processing until a content of the change of the target position is determined.
Figure 18:
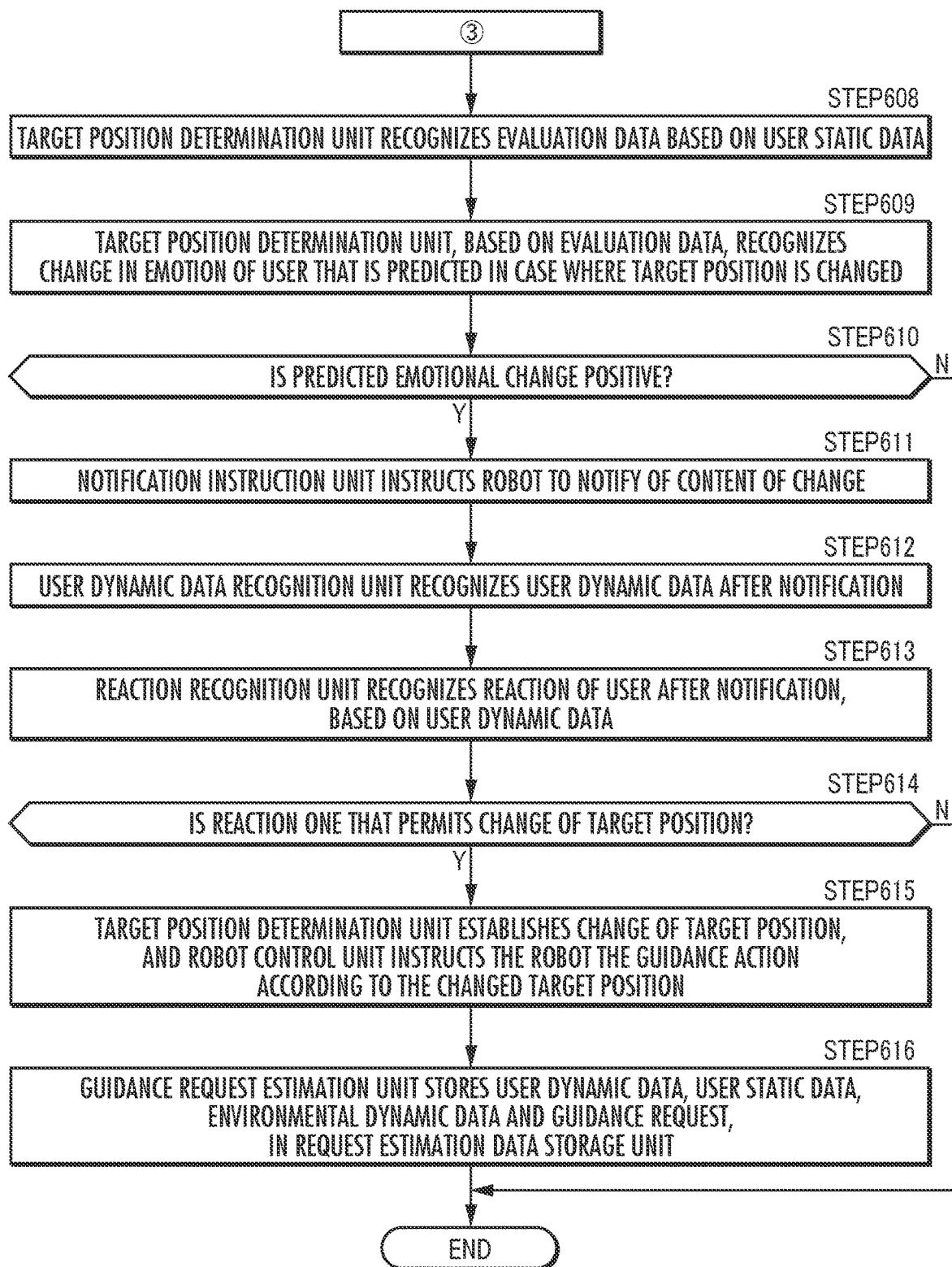
FIG. 18 is a flowchart illustrating, of the processing that the guidance system of FIG. 1 performs when changing a target position during guidance, processing until the change of the target position is executed.

FIG. 15 is a flowchart illustrating the processing that the server 3 of the guidance system S performs when determining the target position immediately after the start of the guidance. Furthermore, FIG. 17 is a flowchart illustrating, of the processing that the server 3 of the guidance system S performs when changing the target position during the guidance, processing until a content of the change of the target position is determined. Furthermore, FIG. 18 is a flowchart illustrating, of the processing that the server 3 of the guidance system S performs when changing the target position during the guidance, processing until the change of the target position is executed.

First, the processing that the guidance system S performs when determining the target position immediately after the start of the guidance will be described.

In this processing, the user static data recognition unit 3a2 of the data recognition unit 3a of the server 3 first recognizes the user static data before the start of the guidance (STEP 501 in FIG. 15).

Specifically, similarly to the processing in STEP 101 in FIG. 7 and STEP 301 in FIG. 11, the reception terminal 1 first recognizes information input by the user at the time of reception, information on the reception terminal 1 that has accepted the reception, and the result of the questionnaire to the user performed via the output unit of the reception terminal 1, and transmits these pieces of information to the server 3.

Thereafter, the user static data recognition unit 3a2 acquires, the information transmitted from the reception terminal 1, information that may affect the determination of the target position, and recognizes the information as the user static data.

As the information that may affect the determination of the target position in this processing, for example, there may be mentioned information mainly on attributes of the user such as presence or absence of physical (in particular, eyes, ears) disability, use or non-use of a wheelchair, handedness, presence or absence of companion, pregnancy status, and a past use history.

Next, the target position determination unit 3f3 of the guidance action determination unit 3f of the server 3 determines a first position being the target position at the start of the guidance, based on the recognized user static data (STEP 502 in FIG. 15).

In the present embodiment, as illustrated in FIG. 14, a position that is outside a personal area of a user U, in front of the user U, and near a peripheral field-of-view area of a central field-of-view area of the user U (that is, a position diagonally in front of the user U) is the first position. Here, a distance and direction (which of the left and right sides of the user it is located on) of the first position are determined depending on handedness of the user, presence or absence of eye or ear disability of the user, and the like that are included in the user static data.

The first position may be determined by referring to the evaluation data in addition to the user static data or, in the case where a past use history of the user is present, may use the target position in the past use history.

Next, the robot control unit 3j of the server 3 issues to the robot 2 an instruction for the guidance action (STEP 503 in FIG. 15).

Specifically, for example, the robot control unit 3j transmits to the robot 2 an instruction for guiding the user along the guidance route at the start of the guidance determined in the processing described with reference to FIG. 7 (the second route R2 of FIG. 8) or along the changed guidance route determined in the processing described with reference to FIGS. 9 and 10 (the third route R3 of FIG. 8), at the guidance speed at the start of the guidance determined in the processing described with reference to FIG. 11 or at the changed guidance speed determined in the processing described with reference to FIGS. 12 and 13.

The robot 2 that has received the instruction moves to around the user (that is, the guidance start location P0) and then starts the guidance. In the present embodiment, the time point when the robot 2 starts to move is the guidance start time point. Furthermore, after the start of the guidance, after the robot 2 once moves to the target position determined based on the user static data, the relative position is not adjusted at this stage, and the robot 2 moves at a constant speed (for example, the second speed determined in the processing described with reference to FIG. 11).

Next, the relative position recognition unit 3b of the server 3 recognizes the relative position of the robot 2 with respect to the user (STEP 504 in FIG. 15).

Specifically, the robot 2 first transmits to the server 3 data on an image of the user captured by the second camera 22d of the robot 2. Thereafter, the relative position recognition unit 3b recognizes, as the relative position, the distance from the user to the robot and the direction in which the robot is located with respect to the user, based on the information transmitted to the server 3. This processing is sequentially executed at a predetermined processing cycle after the start of the guidance.

Next, the target position determination unit 3f3 of the guidance action determination unit 3f of the server 3 recognizes a variation amount in the relative position (STEP 505 in FIG. 15).

Figure 16:
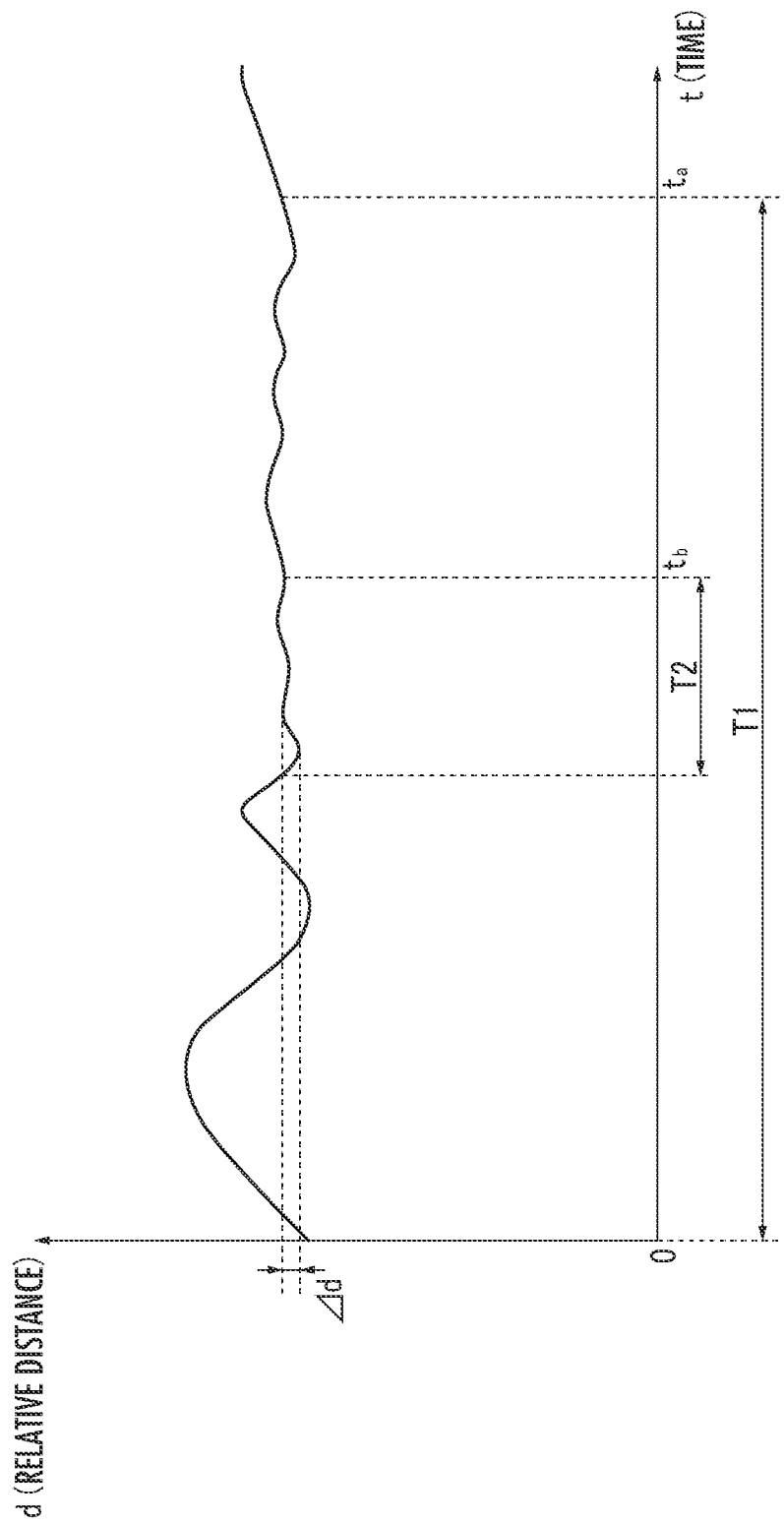
FIG. 16 is a graph illustrating an example of a change in relative distance between the user and the robot, in which the horizontal axis indicates time and the vertical axis indicates the relative distance.

Specifically, every time the relative position recognition unit 3b recognizes the relative position, the target position determination unit 3f3 calculates the variation amount in the distance and the direction in this recognition with respect to the distance and the direction in the previous recognition and records the calculated variation amount in time series. As a result, regarding the variation amount, data as in a graph illustrated in FIG. 16 is obtained. In this graph, t indicates the time, d indicates the relative distance, and Δd indicates the variation amount.

Next, the target position determination unit 3f3 determines whether the variation amount is equal to or less than a predetermined value (STEP 506 in FIG. 15).

This predetermined value may be optionally set by the system designer of the guidance system S or the like. For example, based on the user static data and the evaluation data, a value determined from an attribute of the user to be guided and a past guidance result may be set as the predetermined value.

When it is determined that it exceeds the predetermined value (in the case of NO in STEP 506 in FIG. 15), the processing returns to STEP 504, and the relative position recognition unit 3b recognizes the relative position again.

On the other hand, when it is determined that it is equal to or less than the predetermined value (in the case of YES in STEP 506 in FIG. 15), the target position determination unit 3f3 determines whether remaining time until a first time elapses from when the user starts to move after the robot 2 starts the guidance is equal to or more than a second time (STEP 507 in FIG. 15).

The first time and the second time may be optionally set by the system designer of the guidance system S or the like, as long as the first time is longer than the second time. In the present embodiment, the first time is 60 seconds and indicated as T1 in the graph of FIG. 16. Furthermore, the second time is 15 seconds and indicated as T2 in the graph illustrated in FIG. 16.

Furthermore, the start time point of the first time, which is the guidance start time point in the present embodiment, may be any different time point that is after the guidance start time point. For example, the time point when the user starts to move may be the start time point, or the time point when a predetermined time (for example, 10 seconds) elapses from the start of the guidance may be the start time point.

This processing in STEP 507 determines whether, based on ta denoting the time point when the first period T1 ends, tb denoting the time point when the second period T2 ends is an earlier time point or a later time point (that is, whether the second time ends during a reference position determination period, which will be described later).

On the other hand, when it is determined that it is equal to or more than the second time (in the case of YES in STEP 507 in FIG. 15), the target position determination unit 313 determines whether the time during which the variation amount in the state of being equal to or less than the predetermined value is maintained is equal to or more than the second time (STEP 508 in FIG. 15).

When it is determined that it is less than the second time (in the case of NO in STEP 508 in FIG. 15), the processing returns to STEP 504, and the relative position recognition unit 3b recognizes the relative position again.

On the other hand, when it is determined that it is equal to or more than the second time (in the case of YES in STEP 508 in FIG. 15), the target position determination unit 3f3 determines the target position during the guidance, based on the relative position during the second time (STEP 509 in FIG. 15).

Specifically, for example, the target position determination unit 33 determines an average value of the relative position measured during the second time, as a second position being the target position during the guidance.

On the other hand, when it is determined that it is less than the second time (in the case of NO in STEP 507 in FIG. 15), the target position determination unit 3f3 determines the target position at the start of the guidance as the target position during the guidance (STEP 510 in FIG. 15).

Specifically, the target position determination unit 3f3 determines the first position being the target position at the start of the guidance as the second position being the target position during the guidance.

Next, the robot control unit 3j issues to the robot 2 an instruction for the guidance action according to the determined target position and ends this processing (STEP 511 in FIG. 15).

Specifically, for example, the robot control unit 3j transmits to the robot 2 an instruction for moving the robot 2 such that the relative position becomes the determined target position.

Although in STEPs 501 to 511 above, the processing until the distance included in the relative position is determined has been described, the direction included in the relative position is also determined by the similar processing.

As described above, in the guidance system S, the target position is determined based on the relative position recognized when the user starts to move after the robot 2 starts the guidance (that is, at the start of the guidance). This is because the present inventor, as a result of earnest studies, has obtained the finding that the target position is less stressful for the user.

Thus, according to the guidance system S, the position at which the user is less likely to feel stress is the target position, so that the user can receive the guidance with less stress.

In the guidance system S, the period until the first time elapses from when the user starts to move after the robot 2 starts the guidance is the reference position determination period (in the graph of FIG. 16, the period from t=0 to t=tb).

Then, in the guidance system S, as illustrated as the processing in STEPs 506 to 509, the relative position is sequentially recognized during the reference position determination period, and when, during the reference position determination period, the state where the variation amount (Δd) in the relative position is equal to or less than the predetermined value is continued for equal to or more than the second time, the target position is determined based on the relative position during the second time.

This is because the walking start timing when the user starts to move after the robot 2 starts the guidance may differ depending on the same user. For example, in the case of missing the start of the guidance by the robot 2, the walking start timing is delayed, as a matter of course. As a result, the relative position recognized at the start of the guidance may become different from the relative position considered to be originally preferable.

Accordingly, as described above, in the case where the target position is determined based on the relative position recognized during a predetermined period and the variation amount in the relative position, the influence of a change in such a walking start timing is suppressed, so that a suitable target position can be determined.

However, the present invention is not limited to such a configuration, and the target position may not be determined based on the position recognized during a predetermined period and the variation amount in the relative position. For example, the target position may be determined based on the relative position at a time point after elapse of a predetermined period from the timing at which the user starts to walk.

Next, the processing that the server 3 of the guidance system S performs when changing the target position during the guidance will be described.

In this processing, the user dynamic data recognition unit 3a1 of the data recognition unit 3a of the server 3 first recognizes current user dynamic data (STEP 601 in FIG. 17).

Specifically, similarly to the processing in STEP 201 in FIG. 9 and STEP 401 in FIG. 12, the user dynamic data recognition unit 3a1 recognizes, as the user dynamic data, a behavior of the user (for example, an expression, movement of the line of sight) during the guidance, biological information (for example, a physical condition, a degree of fatigue), and the like, based on the information transmitted from the robot 2.

Next, the environmental dynamic data recognition unit 3a3 of the data recognition unit 3a of the server 3 recognizes the environmental dynamic data on the current location of the robot 2 (consequently, the current location P2 of the user) (STEP 602 in FIG. 17).

Specifically, similarly to the processing in STEP 203 in FIG. 9 and STEP 402 in FIG. 12, the environmental dynamic data recognition unit 3a3 acquires, of the information transmitted from the robot 2, information that may affect the change of the target position, and recognizes the information as the environmental dynamic data.

As the information that may affect the change of the target position in this processing, for example, there may be mentioned information on a degree of congestion in the vicinity of the user during the guidance, a magnitude of noise in the vicinity of the user, a size of a passage, and a traffic rule in the route during the guidance.

This is because, for example, in the case where the vicinity of the user is congested, it is necessary to bring the robot 2 closer to the user such that the user does not lose sight of the robot 2.

Furthermore, this is because, for example, in the case where noise in the vicinity of the user is large, it is necessary to approach the user such that a voice of the user can be easily acquired or such that a sound from the robot 2 can be easily conveyed to the user.

Furthermore, this is because, for example, in the case where the size of the passage is narrow, it is difficult to cause the robot 2 to be located at a position diagonally in front of the user, and thus it is necessary to move the robot 2 to the front side of the user.

Furthermore, this is because, for example, in a place where, for example, a stop is required as a traffic rule, it is preferable that the robot 2 is located next to the user so as not to interfere with the user when the movement resumes.

Next, the user dynamic data recognition unit 3a1 determines whether the recognized user dynamic data is predetermined user dynamic data set in advance (STEP 603 in FIG. 17).

Specifically, similarly to the processing in STEP 202 in FIG. 9 and STEP 403 in FIG. 12, the system designer or the like sets in advance the user dynamic data that should be used as a trigger of the change of the guidance content, and the user dynamic data recognition unit 3a1 determines whether the recognized user dynamic data corresponds to the predetermined user dynamic data set in advance.

As the predetermined user dynamic data, for example, there may be mentioned information indicating that the line of sight of the user has moved to look for something or is focusing on some point, information indicating that the movement direction or movement speed of the user is changed, and information indicating that the user has uttered a voice that conveys a request (for example, want to come nearer).

When it is determined that it is not the predetermined user dynamic data (in the case of NO in STEP 603 in FIG. 17), the environmental dynamic data recognition unit 3a3 determines whether the recognized environmental dynamic data is predetermined environmental dynamic data set in advance (STEP 604 in FIG. 17).

Specifically, similarly to the processing in STEP 404 in FIG. 12, the system designer or the like sets in advance the environmental dynamic data that should be used as a trigger of the change of the guidance content, and the environmental dynamic data recognition unit 3a3 determines whether the recognized environmental dynamic data corresponds to the predetermined environmental dynamic data set in advance.

As such environmental dynamic data, for example, there may be mentioned information indicating a degree of congestion, unscheduled construction, and an event such as a sudden accident.

When it is determined that it is not the predetermined environmental dynamic data (in the case of NO in STEP 604 in FIG. 17), the server 3 executes the processing of STEPs 601 to 604 again.

On the other hand, when it is determined that it is the predetermined user dynamic data (in the case of YES in STEP 603 in FIG. 17), or when it is determined that it is the predetermined environmental dynamic data (in the case of YES in STEP 604 in FIG. 17), the guidance request estimation unit 3c of the server 3 recognizes the request estimation data based on the recognized user static data (STEP 605 in FIG. 17).

Specifically, similarly to the processing in STEP 105 in FIG. 7, STEP 205 in FIG. 9, STEP 305 in FIG. 11, and STEP 405 in FIG. 12, the guidance request estimation unit 3c, based on the data indicating the attribute of the user recognized from the user static data recognized before the start of the guidance (the user static data recognized in STEP 501 in FIG. 15), acquires from the request estimation data storage unit 3d the request estimation data associated with an attribute same as or relating to the attribute.

Next, the guidance request estimation unit 3c estimates the guidance request of the user at the current time point, based on the recognized user dynamic data, environmental dynamic data, and request estimation data (STEP 606 in FIG. 17).

Specifically, the guidance request estimation unit 3*c* first estimates the guidance request of the user (for example, the user wants the robot 2 to come nearer because it is congested), based on the user dynamic data (an expression, movement of the line of sight, and the like) and the environmental dynamic data (for example, a degree of congestion of the current location).

Thereafter, similarly to the processing in STEP 106 in FIG. 7, STEP 206 in FIG. 9. STEP 306 in FIG. 11, and STEP 406 in FIG. 12, the guidance request estimation unit 3*c* refers to the request estimation data, and establishes the estimated guidance request as the guidance request of the user or estimates the guidance request of the user again.

Next, the target position determination unit 3*f*3 of the guidance action determination unit 3*f* of the server 3 determines the content of the change of the target position, based on the estimated guidance request (STEP 607 in FIG. 17).

Specifically, the target position determination unit 3*f*3 determines the content of the change of the target position, according to a rule set in advance by the system designer or the like.

As the rule, for example, there may be mentioned one in which, according to highness or lowness of the degree of congestion, the distance is adjusted (for example, the robot 2 is brought closer to the user as the degree of congestion is higher) and the direction is adjusted (for example, the robot 2 is located in front of the user as the degree of congestion is higher).

Furthermore, for example, there may be mentioned one in which in the case where noise in the vicinity of the user is large, the robot 2 is moved so as to bring the second microphone 22*b* or second speaker 22*c* of the robot 2, or the like closer to the user such that a voice of the user can be easily acquired or such that a sound from the robot 2 can be easily conveyed to the user.

Furthermore, for example, there may be mentioned one in which in the case where the size of the passage is narrower than a predetermined size, it is difficult to cause the robot 2 to be located at a position diagonally in front of the user, and thus the robot 2 is moved to the front side of the user.

Furthermore, for example, there may be mentioned one in which, in a place where, for example, a stop is required as a traffic rule, the robot 2 is moved to next to the user so as not to interfere with the user when the movement resumes.

Next, the target position determination unit 3*f*3 recognizes the evaluation data from the evaluation data storage unit 3*l* based on the recognized user static data (STEP 608 in FIG. 18).

Specifically, similarly to the processing in STEP 212 in FIG. 10 and STEP 411 in FIG. 13, the target position determination unit 33, based on the data indicating the attribute of the user recognized from the user static data recognized before the start of the guidance (the user static data recognized in STEP 501 in FIG. 15), acquires from the evaluation data storage unit 3*l* the evaluation data associated with an attribute same as or relating to the attribute.

Next, the target position determination unit 33, based on the evaluation data, recognizes a change in the emotion of the user that is predicted in the case where the target position is changed (STEP 609 in FIG. 18).

Specifically, similarly to the processing in STEP 213 in FIG. 10 and STEP 412 in FIG. 13, the target position determination unit 33, based on a motion of the robot 2 scheduled to be performed for this guidance request (for example, movement for the change of the target position), recognizes the evaluation data associated with the motion and recognizes the change in the emotion included in the evaluation data.

Next, the target position determination unit 3*f*3 determines whether the predicted emotional change is positive (STEP 610 in FIG. 18).

When it is determined that it is not positive (in the case of NO in STEP 610 in FIG. 18), the server 3 ends this processing without performing the subsequent processing.

On the other hand, when it is determined that it is positive (in the case of YES in STEP 610 in FIG. 18), the notification instruction unit 3*h* of the server 3 instructs the robot 2 to notify of the content of the change (STEP 611 in FIG. 18).

Specifically, for example, in the case of processing relating to the change of the target position, the notification instruction unit 3*h* first instructs the robot 2 to notify of information on the change of the target position such as the fact that the target position is to be changed, and the mason for changing the target position (that is, the estimated guidance request), and inquiry information for inquiring about necessity of the change of the target position.

Thereafter, the robot 2 that has received this instruction performs the notification via the second touch panel 22*a* and the second speaker 22*c* that serve as the output unit.

Next, the user dynamic data recognition unit 3*a*1 recognizes the user dynamic data after the notification of the inquiry information (STEP 612 in FIG. 18).

Specifically, similarly to the processing in STEP 216 in FIG. 9 and STEP 415 in FIG. 13, the user dynamic data recognition unit 3*a*1 recognizes, as the user dynamic data, a behavior of the user after the notification of the inquiry information, and the like, based on the information transmitted from the robot 2.

Next, the reaction recognition unit 3*i* of the server 3 recognizes a reaction of the user, based on the user dynamic data recognized after the notification of the inquiry information (STEP 613 in FIG. 18).

Specifically, similarly to the processing in STEP 217 in FIG. 9 and STEP 416 in FIG. 13, for example, the reaction recognition unit 3*i* recognizes the reaction of the user (specifically, whether the change of the target position is permitted), depending on whether the user dynamic data recognized after the notification corresponds to the behavior set in advance.

Next, the target position determination unit 3*f*3 determines whether the reaction recognized by the reaction recognition unit 3*i* is a reaction that permits the change of the target position (STEP 614 in FIG. 18).

When it is determined that it is not a reaction that permits the change of the target position (in the case of NO in STEP 614 in FIG. 18), the server 3 ends this processing without performing the subsequent processing.

On the other hand, when it is determined that it is a reaction that permits the change of the target position (in the case of YES in STEP 614 in FIG. 18), the target position determination unit 3*f*3 establishes the change of the target position, and the robot control unit 3*j* of the server 3 issues to the robot 2 an instruction for the guidance action according to the changed target position (STEP 615 in FIG. 18).

Specifically, the robot control unit 3*j* transmits to the robot 2 an instruction for moving to the changed target position.

Last, the guidance request estimation unit 3*c* associates, with the estimated guidance request, the user dynamic data used at the time of the estimation of this guidance request (that is, the user dynamic data recognized in STEP 601 in FIG. 17), the environmental dynamic data (that is, the environmental dynamic data recognized in STEP 602 in FIG. 17), and the user static data, stores them in the request estimation data storage unit 3*d*, and ends this processing (STEP 616 in FIG. 18).

In the server 3 configured as described above, during the guidance (specifically, during the period from the start of the guidance to the end of the guidance), the target position is changed based on the estimated guidance request of the user. That is, the target position is changed based on not only a request clearly expressed by the user but also a request that the user potentially has.

As a result, the target position becomes suitable for the guidance request of the user. For example, discomfort due to congestion is taken into consideration.

Thus, according to the guidance system S comprising this server 3 and the guide robot control method using the same, the target position corresponds to the guidance request of the user, and the change of the target position is performed while respecting the user's intention, so that the user can receive the guidance with less stress.

In the processing for the change of the target position in the present embodiment, the user dynamic data is detected sequentially, and the guidance request is accordingly estimated again to perform the change of the target position. This is to sequentially grasp the guidance request of the user that changes from moment to moment so as to suitably change the target position.

However, the present invention is not limited to such a configuration. For example, the recognition of the user dynamic data, the estimation of the guidance request, and consequently the change of the target position may be performed only at a predetermined timing (for example, a timing of passing through a predetermined location, a timing at which a predetermined time elapses).

Furthermore, for example, the recognition of the user dynamic data, the estimation of the guidance request, and consequently the change of the target position may be performed only when, instead of the user dynamic data, the environmental dynamic data is recognized sequentially and predetermined environmental dynamic data is recognized (for example, when the degree of congestion becomes equal to or higher than a predetermined degree).

Furthermore, in the present embodiment, the target position at the start of the guidance is determined by referring to a variation in the relative position during the reference position determination period.

However, the present invention is not limited to such a configuration. For example, instead of the reference position determination period, a reference position determination section (for example, a section from the guidance start location to the first turn) may be set, and the target position at the start of the guidance may be determined by referring to a variation in the relative position during movement in the section.

Furthermore, in the present embodiment, when it is determined that the emotional change that is predicted in the case where the target position is changed is not positive (in the case of NO in STEP 610 in FIG. 18), and when it is determined that the reaction after the notification is not a reaction indicating a permission (in the case of NO in STEP 614 in FIG. 18), the server 3 ends the processing without performing the subsequent processing. This is to give priority to guiding the user to the destination at the desired arrival time, and to give priority to a direct desire of the user.

However, the present invention is not limited to such a configuration. For example, when the recognized user dynamic data includes a direct instruction (for example, when the robot is instructed to be located nearer), or the like, the change of the target position may be executed without performing the determination on the emotional change.

Furthermore, in the present embodiment, the determination of the target position is performed when movement on the guidance route is started. However, the present invention is not limited to such a configuration. For example, when the user drops in any of facilities during the guidance, the target position determined and changed until the facility is reached may be used continuously, while the determination of the target position may be performed again at the time point when the movement is resumed from the facility.

Furthermore, in the present embodiment, when the user dynamic data corresponds to the predetermined user dynamic data, or when the environmental dynamic data corresponds to the predetermined environmental dynamic data, the change of the target position during the guidance is performed.

However, the present invention is not limited to such a configuration, and the change of the target position during the guidance may be performed by referring to the environmental static data. For example, in the case of moving through a narrow passage, the target position may be changed to in front of the front side of the user, not diagonally in front of the user. In the case of performing the change, it is preferable to notify in advance that the change is to be performed.

Next, processing that the guidance system S performs when estimating evaluation of the user will be described with reference to FIGS. 5, 6, 19, and 20.

FIG. 19 is a flowchart illustrating the processing that the server 3 of the guidance system S performs when estimating the evaluation.

In this processing, the user static data recognition unit 3*a*2 of the data recognition unit 3*a* of the server 3 first recognizes the user static data before the start of the guidance (STEP 701 in FIG. 19).

Specifically, similarly to the processing in STEP 101 in FIG. 7. STEP 301 in FIG. 11, and STEP 501 in FIG. 15, the reception terminal 1 first recognizes information input by the user at the time of reception, information on the reception terminal 1 that has accepted the reception, and the result of the questionnaire to the user performed via the output unit of the reception terminal 1, and transmits these pieces of information to the server 3.

Thereafter, the user static data recognition unit 3*a*2 acquires, the information transmitted from the reception terminal 1, information on attributes of the user, and recognizes the information as the user static data. As the attributes of the user in this processing, for example, there may be mentioned age, gender, and desired arrival time.

Next, the user dynamic data recognition unit 3*a*1 of the data recognition unit 3*a* of the server 3 recognizes the user dynamic data before the start of the guidance (STEP 702 in FIG. 19).

Specifically, similarly to the processing in STEP 104 in FIG. 7, the user dynamic data recognition unit 3*a*1 recognizes, as the user dynamic data, a behavior of the user at the start of the guidance, biological information (for example, a physical condition, a degree of fatigue), and the like, based on the information transmitted from the reception terminal 1.

Next, the emotion estimation unit 3*k* of the server 3 estimates a reference emotion based on the recognized user dynamic data before the start of the guidance (STEP 703 in FIG. 19).

Specifically, for example, the emotion estimation unit 3k first estimates which of the areas of the Plutchik emotion model M illustrated in FIG. 6 the emotion of the user at the time of reception belongs to, based on the recognized user dynamic data before the start of the guidance. Then, the area is used as the reference emotion. Furthermore, at this time, the area to which the reference emotion belongs is set to 0, and the emotion estimation unit 3k sets a score for each of the other areas.

Next, the robot control unit 3j of the server 3 issues to the robot 2 an instruction for the guidance action (STEP 704 in FIG. 19).

Specifically, for example, the robot control unit 3j transmits to the robot 2 an instruction for guiding the user along the guidance route at the start of the guidance determined in the processing described with reference to FIG. 7 (the second route R2 of FIG. 8) or along the changed guidance route determined in the processing described with reference to FIGS. 9 and 10 (the third route R3 of FIG. 8), at the guidance speed at the start of the guidance determined in the processing described with reference to FIG. 11 or at the changed guidance speed determined in the processing described with reference to FIGS. 12 and 13, with the target position determined in the processing described with reference to FIG. 15 or the changed target position determined in the processing described with reference to FIGS. 17 and 18 as the target position of the relative position.

The robot 2 that has received the instruction moves to around the user (that is, the guidance start location P0) and then starts the guidance. In the present embodiment, the location point within a predetermined range with its center as the user and to which the robot 2 has moved so as to be located in front of the user is the guidance start location point.

Next, the user dynamic data recognition unit 3a1 recognizes current user dynamic data (STEP 705 in FIG. 19).

Specifically, similarly to the processing in STEP 201 in FIG. 9, STEP 401 in FIG. 12, and STEP 601 in FIG. 17, the user dynamic data recognition unit 3a1 recognizes, as the user dynamic data, a behavior of the user during the guidance (for example, an expression, movement of the line of sight), biological information (for example, a physical condition, a degree of fatigue), and the like, based on the information transmitted from the robot 2.

Next, the user dynamic data recognition unit 3a1 determines whether the recognized current user dynamic data is predetermined user dynamic data set in advance (STEP 706 in FIG. 19).

Specifically, similarly to the processing in STEP 202 in FIG. 9, STEP 403 in FIG. 12, and STEP 603 in FIG. 17, the system designer or the like sets in advance the user dynamic data that should be used as a trigger of the change of the guidance content, and the user dynamic data recognition unit 3a1 determines whether the recognized user dynamic data corresponds to the predetermined user dynamic data set in advance.

As the predetermined user dynamic data, for example, there may be mentioned information indicating that the line of sight of the user has moved to look for something or is focusing on some point, information indicating that the movement direction or movement speed of the user is changed, and information indicating that the user has uttered a voice that conveys a request.

Next, the emotion estimation unit 3k determines whether a current motion of the robot 2 is a predetermined motion set in advance (STEP 707 in FIG. 19).

Specifically, the system designer or the like sets in advance a motion of the robot 2 that should be used as a trigger of the change of the guidance content, and the emotion estimation unit 3k recognizes a motion of the robot 2 based on a signal from the robot 2 and determines whether the recognized motion corresponds to the predetermined motion set in advance.

The predetermined motion includes, for example, change of the guidance route, the guidance speed, or the target position, and a motion intentionally performed by the robot 2 such as notification associated therewith. Furthermore, the predetermined motion also includes, for example, in the case where the robot 2 performs a humanlike motion in a pseudo manner, a motion corresponding to a bow, and the like.

Furthermore, the predetermined motion also includes a motion unintentionally performed by the robot 2. Specifically, it also includes a motion in which the robot 2 has become too close to the user or too far from the user according to a change in the movement speed of the user or the like.

When it is determined that it is not the predetermined motion (in the case of NO in STEP 707 in FIG. 19), the server 3 executes the processing of STEPs 705 to 707 again.

On the other hand, when it is determined that it is the predetermined user dynamic data (in the case of YES in STEP 706 in FIG. 19), or when it is determined that it is the predetermined motion (in the case of YES in STEP 707 in FIG. 19), the emotion estimation unit 3k estimates a current emotion based on the current user dynamic data (STEP 708 in FIG. 19).

Specifically, for example, similarly to the processing in STEP 703 in FIG. 19, the emotion estimation unit 3k estimates which of the areas of the Plutchik emotion model M illustrated in FIG. 6 the current emotion of the user belongs to (that is, the current emotion itself), based on the recognized current user dynamic data.

Furthermore, the eight areas of the emotion model M are classified as either positive or negative. Accordingly, by estimating which of the areas the estimated current emotion belongs to, it is also estimated whether the current emotion is positive or negative.

Furthermore, in the emotion model M, based on the reference emotion, a score is set according to the area and the degree. The emotion estimation unit 3k, after estimating the current emotion, recognizes a variation in the score to thereby also recognize a change in the current emotion with respect to the reference emotion.

Then, the emotion estimation unit 3k recognizes, as the current emotion, not only the current emotion itself but also the one including whether the current emotion is positive or negative and the change in the current emotion with respect to the reference emotion.

Next, the environmental dynamic data recognition unit 3a3 of the data recognition unit 3a of the server 3 recognizes the environmental dynamic data on the current location of the robot 2 (consequently, the current location P2 of the user) (STEP 709 in FIG. 19).

Specifically, similarly to the processing in STEP 203 in FIG. 9, STEP 402 in FIG. 12, and STEP 602 in FIG. 17, it is recognized as the environmental dynamic data by the environmental dynamic data recognition unit 3a3 based on the information transmitted from the robot 2.

Next, the emotion estimation unit 3k stores in the evaluation data storage unit 3l the evaluation data on the current emotion, the user static data, and the environmental dynamic data on the current location (STEP 710 in FIG. 19).

Specifically, the emotion estimation unit 3*k* first associates, with the current emotion estimated by this processing, a motion of the robot 2 performed immediately before the current user dynamic data used as a trigger of the emotion estimation (the user dynamic data used as a determination target in STEP 706 in FIG. 19) is recognized or the motion of the robot 2 used as a trigger of the emotion estimation (the motion used as a determination target in STEP 707 in FIG. 19), and uses them as the evaluation data on the current emotion.

Thereafter, the emotion estimation unit 3*k* associates, with the evaluation data, the user static data recognized in STEP 701 in FIG. 19 and the environmental dynamic data on the current location recognized in STEP 709 in FIG. 19.

Then, the emotion estimation unit 3*k* stores these pieces of evaluation data in the evaluation data storage unit 3*l* in time series (specifically, in association with a time at which the emotion estimation is performed). As a result, regarding the evaluation data, data as in a graph illustrated in FIG. 20 is obtained.

In this graph, the reference emotion is 0, an emotion more positive than the reference emotion is plus, and an emotion more negative than the reference emotion is minus. Furthermore, in this graph, each of t1, t2, t3, t4, and t5 is a time at which the current user dynamic data used as a trigger of the emotion estimation is recognized or a time at which the motion of the robot 2 used as a trigger of the emotion estimation is performed.

For example, in the present embodiment, time of t1 is a time at which a motion indicating the start of the guidance is performed, time of each of t2, t3, and t4 is a time at which the user performs a behavior or the like corresponding to the predetermined user dynamic data or a time at which the robot 2 performs the predetermined motion based on the estimated guidance request, and time of t5 is a time at which at the end of the guidance, the robot 2 performs a motion indicating the end of the guidance.

Next, the emotion estimation unit 3*k* determines whether the guidance has ended (STEP 711 in FIG. 19).

Specifically, for example, the emotion estimation unit 3*k* determines whether the guidance has ended by determining whether the destination is reached or whether the robot 2 has performed a motion indicating the end of the guidance (for example, a hand waving motion after making a bow).

When it is determined that it has not ended (in the case of NO in STEP 711 in FIG. 19), the server 3 executes the processing of STEPs 705 to 711 again.

On the other hand, when it is determined that it has ended (in the case of YES in STEP 711 in FIG. 19), the emotion estimation unit 3*k* stores in the evaluation data storage unit 3*l* the evaluation data on the entire guidance and the user static data (STEP 712 in FIG. 19).

Specifically, the emotion estimation unit 3*k* first creates a graph as illustrated in FIG. 20 based on the evaluation data from the start of the guidance to the end of the guidance, and the emotion estimation unit 3*k* calculates an integral value based on the graph. Thereafter, the emotion estimation unit 3*k* uses, as the evaluation data, the integral value, contents of the guidance (for example, in addition to the guidance route, the guidance speed, and the target position, the environmental dynamic data recognized during the guidance), and all of the motions of the robot 2 during the guidance. Then, the emotion estimation unit 3*k* associates, with the evaluation data, the user static data recognized in STEP 701 in FIG. 19 and stores them in the evaluation data storage unit 3*l*.

In the server 3 configured as described above, the motion of the robot 2 associated with the current emotion of the user estimated based on the behavior of the user at the time of the motion (that is, the user dynamic data) is collected as the evaluation data.

As a result, the collected evaluation data clearly indicates a relevance between the motion of the robot 2 and a change in the emotion of the user (that is, satisfaction), compared with data based on a questionnaire result performed after the end of the guidance, or the like.

Thus, according to the guidance system S comprising this server 3 and the guide robot control method using the same, it is possible to collect evaluation data effective for grasping user's satisfaction with respect to a motion of the robot 2 with high accuracy. Consequently, a motion of the robot 2 is set with reference to the evaluation data, so that the user can receive the guidance with less stress.

In the present embodiment, the reference emotion estimation of the emotion estimation unit 3*k* is performed at the start of the guidance. This is to use the emotion at the start of the guidance as the reference emotion to thereby precisely grasp an emotion with respect to a motion of the robot during the guidance.

However, the emotion estimation unit of the present invention is not limited to such a configuration, and the reference emotion may be set at a timing other than the start of the guidance, or may be set at a plurality of times, not only once. For example, in the case where the user drops in a predetermined facility during the guidance, the reference emotion may be estimated every time the guidance is resumed from the facility. As a result, an influence on the emotion due to an event that has occurred in the facility can be suppressed.

In the present embodiment, a reference emotion is estimated, and based on the reference emotion, a change in the current emotion is recognized. This is because an emotion serving as a reference is set, so that a change in the emotion of the user with respect to each motion of the robot 2 (as a result of the motion, whether it becomes favorable or worse, or the like) is grasped more precisely.

However, the present invention is not limited to such a configuration. For example, a change in emotion with respect to an immediately preceding emotion (that is, simply a change in emotion at each moment) may be recognized without using the reference emotion.

Furthermore, in the present embodiment, the emotion estimation unit 3*k*, at the end of the guidance, includes, in the evaluation data on the entire guidance, the integral value of the change in the current emotion as a change in the emotion with respect to the entire guidance, and stores them in the evaluation data storage unit 3*l*. This is to grasp not only individual motions of the robot 2 but also evaluation for the entire guidance.

However, the present invention is not limited to such a configuration. For example, the current emotion at the end of the guidance itself or a result of comparison between the current emotion at the end of the guidance and the reference emotion may be used as the change in the emotion with respect to the entire guidance. Furthermore, the change in the emotion with respect to the entire guidance may not be included in the evaluation data.

Although the embodiment illustrated in the drawings has been described above, the present invention is not limited to such an embodiment.

For example, in the embodiment, determination of a guidance route, a guidance speed, and a target position is performed according to an estimated guidance request.

However, the guidance action of the present invention is not limited to this and may also include other motions that the robot performs during the guidance.

For example, it may also include contents of services provided via the robot such as music delivered by the robot during the guidance and a content of advertisement presented by the robot, in addition to motions of the robot itself such as sound, sound effect, and signal sound of the robot at the time of the guidance, type, sound emission frequency, and sound volume of music delivered from the robot at the time of the guidance, and motion patterns of the robot (for example, moving in a curved manner, moving in a linear manner).

REFERENCE SIGNS LIST

1: reception terminal, 1$a$: first touch panel, 1$b$: keyboard, 1$c$: first microphone, 1$d$: first speaker, 1$e$: first camera, 2: robot, 3: server (guide robot control device), 3$a$: data recognition unit, 3$a$1: user dynamic data recognition unit, 3$a$2: user static data recognition unit, 3$a$3: environmental dynamic data recognition unit, 3$a$4: environmental static data recognition unit, 3$b$: relative position recognition unit, 3$c$: guidance request estimation unit, 3$d$: request estimation data storage unit, 3$e$: map storage unit, 3$f$: guidance action determination unit, 3$f$1: route determination unit, 3$f$2: guidance speed determination unit, 33: target position determination unit, 3$g$: priority storage unit, 3$h$: notification instruction unit, 3$i$: reaction recognition unit, 3$j$: robot control unit, 3$k$: emotion estimation unit, 3$l$: evaluation data storage unit, 4: monitoring system, 20: lower base, 20$a$: first actuator, 20$b$: second actuator, 20$c$: third actuator, 21: moving motion unit, 21$a$: core body, 21$b$: roller, 22: upper base, 22$a$: second touch panel, 22$b$: second microphone, 22$c$: second speaker, 22$d$: second camera, 23: control device, 24: communication device, 25: acceleration sensor, 26: position sensor, A1: first area, A2: second area, A3: third area, A4: fourth area, A5: fifth area, A6: sixth area, A7: seventh area, A8: eighth area, C1: first center, C2: second center, L1: first virtual line, L2: second virtual line, M: emotion model, P0: guidance start location, P1: destination, P2: current location, P3: event venue, P4: store, R1: first route, R2: second route, R3: third route, S: guidance system, U: user

The invention claimed is:

1. A guide robot control device for controlling a robot configured to move with a user and guide the user to a destination, the device comprising:
a route determination unit configured to determine a route from a current location of the user to the destination;
a user dynamic data recognition unit configured to, during guidance, recognize user dynamic data which is information on the user, the information changing over time;
a guidance request estimation unit configured to estimate a guidance request of the user, based on the user dynamic data;
a notification instruction unit configured to issue to the robot an instruction for notification of inquiry information to the user using an output unit of the robot for inquiring about necessity of change of the route, based on the determined route, wherein the output unit of the robot comprises at least one of a touch panel and a speaker; and
a reaction recognition unit configured to recognize a reaction of the user to the notification based on the instruction,
wherein the route determination unit is configured to determine a content of the change of the route, based on the estimated guidance request, and determine whether or not to perform the change of the route, based on the reaction.

2. The guide robot control device according to claim 1, wherein the route determination unit is configured to estimate a change in required time of the route before and after the change, and
the notification instruction unit is configured to issue an instruction for notification of at least one of the change in the required time and arrival time to the destination in a case where the route is changed.

3. The guide robot control device according to claim 1, wherein the user dynamic data is data including at least one of a behavior of the user and biological information of the user.

4. The guide robot control device according to claim 3, wherein the behavior of the user includes at least one of a movement speed of the user, a posture of the user, an expression of the user, an utterance of the user, and a motion of a predetermined portion of a body of the user.

5. The guide robot control device according to claim 3, wherein the biological information of the user includes at least one of a body temperature of the user, a sweating state of the user, and an emotion of the user estimated based on at least one of the body temperature of the user, the sweating state of the user, and the behavior of the user.

6. The guide robot control device according to claim 1, comprising
a priority storage unit configured to store priority on facilities in a guidance area,
wherein the route determination unit is configured to perform the change of the route, based on the estimated guidance request and the priority.

7. A guidance system comprising:
a robot configured to move with a user and guide the user to a destination; and
the guide robot control device according to claim 1,
wherein the guide robot control device has a robot control unit configured to move the robot along the route.

8. A guide robot control method for controlling a robot configured to move with a user and guide the user to a destination, the method comprising:
a step in which a route determination unit determines a route from a current location of the user to the destination;
a step in which a user dynamic data recognition unit recognizes, during guidance, user dynamic data which is information on the user, the information changing over time;
a step in which a guidance request estimation unit estimates a guidance request of the user, based on the user dynamic data;
a step in which a notification instruction unit issues to the robot an instruction for notification of inquiry information to the user using an output unit of the robot for inquiring about necessity of change of the route, based on the determined route, wherein the output unit of the robot comprises at least one of a touch panel and a speaker;
a step in which a reaction recognition unit recognizes a reaction of the user to the notification based on the instruction;
a step in which the route determination unit determines a content of the change of the route, based on the estimated guidance request; and a step in which the route determination unit determines whether or not to perform the change of the route, based on the reaction.

\* \* \* \* \*